United States Patent
Zapol et al.

(10) Patent No.: US 10,279,139 B2
(45) Date of Patent: May 7, 2019

(54) SYNTHESIS OF NITRIC OXIDE GAS FOR INHALATION

(71) Applicant: THE GENERAL HOSPITAL CORPORATION, Boston, MA (US)

(72) Inventors: Warren M. Zapol, Cambridge, MA (US); Binglan Yu, Lexington, MA (US); Paul Hardin, Lowell, MA (US); Matthew Hickcox, Groton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/880,018

(22) Filed: Jan. 25, 2018

(65) Prior Publication Data

US 2018/0221619 A1    Aug. 9, 2018

Related U.S. Application Data

(63) Continuation of application No. 14/777,084, filed as application No. PCT/US2014/027986 on Mar. 14, 2014.

(Continued)

(51) Int. Cl.
*A61M 16/10* (2006.01)
*C01B 21/20* (2006.01)
(Continued)

(52) U.S. Cl.
CPC ........... *A61M 16/12* (2013.01); *A61M 15/02* (2013.01); *A61M 16/0003* (2014.02);
(Continued)

(58) Field of Classification Search
CPC .............. A61M 15/02; A61M 15/0016; A61M 15/0091; A61M 16/10; A61M 16/104;
(Continued)

(56) References Cited

U.S. PATENT DOCUMENTS 2,485,481 A    10/1949    Cotton
2,525,938 A    10/1950    Peck
(Continued)

FOREIGN PATENT DOCUMENTS

CN    1099997 A    3/1995
CN    1730115 A    2/2006
(Continued)

OTHER PUBLICATIONS

Mok, et al., Application of Positive Pulsed Corona Discharge to Removal of SO2 and NOx, Proceedings, ICESP VII, Sep. 20-25, 1998, Kyongju, Korea, 8 pages.
(Continued)

*Primary Examiner* — Michael J Tsai
(74) *Attorney, Agent, or Firm* — Quarles & Brady LLP

(57) ABSTRACT

In some additional aspects, an apparatus can include a chamber having an inlet valve for receiving a reactant gas and an outlet valve for delivering a product gas, a piston positioned inside the chamber and configured to move along a length of the chamber for adjusting pressure in the chamber, a sensor for collecting information related to one or more conditions of a respiratory system associated with a patient, a controller for determining one or more control parameters based on the collected information, and one or more pairs of electrodes positioned inside the chamber for initiating a series of electric arcs external to the patient to generate nitric oxide based on the determined control parameters.

21 Claims, 26 Drawing Sheets

Related U.S. Application Data

(60) Provisional application No. 61/789,161, filed on Mar. 15, 2013, provisional application No. 61/792,473, filed on Mar. 15, 2013.

(51) Int. Cl.
*A61M 16/12* (2006.01)
*B01D 53/56* (2006.01)
*A61M 16/00* (2006.01)
*A61M 16/04* (2006.01)
*A61M 16/06* (2006.01)
*A61M 16/20* (2006.01)
*A61M 15/02* (2006.01)

(52) U.S. Cl.
CPC .... *A61M 16/0063* (2014.02); *A61M 16/0072* (2013.01); *A61M 16/0465* (2013.01); *A61M 16/06* (2013.01); *A61M 16/10* (2013.01); *A61M 16/101* (2014.02); *A61M 16/20* (2013.01); *B01D 53/56* (2013.01); *C01B 21/203* (2013.01); *A61M 16/0057* (2013.01); *A61M 16/107* (2014.02); *A61M 16/108* (2014.02); *A61M 16/202* (2014.02); *A61M 16/209* (2014.02); *A61M 2016/0021* (2013.01); *A61M 2016/0033* (2013.01); *A61M 2016/1025* (2013.01); *A61M 2016/1035* (2013.01); *A61M 2202/0208* (2013.01); *A61M 2202/0216* (2013.01); *A61M 2202/0275* (2013.01); *A61M 2205/04* (2013.01); *A61M 2205/33* (2013.01); *A61M 2205/3303* (2013.01); *A61M 2205/3334* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/3606* (2013.01); *A61M 2205/366* (2013.01); *A61M 2205/50* (2013.01); *A61M 2205/7545* (2013.01); *A61M 2210/1032* (2013.01); *A61M 2230/40* (2013.01); *B01D 2251/304* (2013.01); *B01D 2251/306* (2013.01); *B01D 2251/404* (2013.01)

(58) Field of Classification Search
CPC .. A61M 2016/0015; A61M 2202/0275; C01B 21/20; C01B 21/203; C01B 21/24; C01B 21/30
See application file for complete search history.

(56) References Cited

U.S. PATENT DOCUMENTS

| | | |
|---|---|---|
| 2,684,448 A | 7/1954 | Nilles, Jr. |
| 3,225,309 A | 12/1965 | Phelps |
| 4,287,040 A | 9/1981 | Alamaro |
| 4,500,563 A | 2/1985 | Ellenberger et al. |
| 4,505,795 A | 3/1985 | Alamaro |
| 4,695,358 A | 9/1987 | Mizuno et al. |
| 4,705,670 A | 11/1987 | O'Hare |
| 4,816,229 A | 3/1989 | Jensen et al. |
| 4,877,589 A | 10/1989 | O'Hare |
| 5,285,372 A | 2/1994 | Huynh et al. |
| 5,378,436 A * | 1/1995 | Endoh ............... C01B 15/0295 204/157.21 |
| 5,396,882 A | 3/1995 | Zapol |
| 5,471,977 A | 12/1995 | Olsson et al. |
| 5,485,827 A | 1/1996 | Zapol et al. |
| 5,546,935 A | 8/1996 | Champeau |
| 5,558,083 A | 9/1996 | Bathe et al. |
| 5,573,733 A | 11/1996 | Salama |
| 5,692,495 A | 12/1997 | Sheu |
| 5,732,693 A | 3/1998 | Bathe et al. |
| 5,752,504 A | 5/1998 | Bathe |
| 5,839,433 A | 11/1998 | Higenbottam |
| 5,845,633 A | 12/1998 | Psaros |
| 6,089,229 A | 7/2000 | Bathe et al. |
| 6,109,260 A | 8/2000 | Bathe |
| 6,125,846 A | 10/2000 | Bathe et al. |
| 6,164,276 A | 12/2000 | Bathe et al. |
| 6,224,653 B1 | 5/2001 | Shvedchikov et al. |
| 6,250,302 B1 | 6/2001 | Rantala |
| 6,296,827 B1 | 10/2001 | Castor et al. |
| 6,536,429 B1 | 3/2003 | Pavlov et al. |
| 6,668,828 B1 | 12/2003 | Figley et al. |
| 6,758,214 B2 | 7/2004 | Fine et al. |
| 6,920,876 B2 | 7/2005 | Miller et al. |
| 6,955,171 B1 | 10/2005 | Figley et al. |
| 6,955,790 B2 | 10/2005 | Castor et al. |
| 6,986,351 B2 | 1/2006 | Figley et al. |
| 7,025,869 B2 | 4/2006 | Fine et al. |
| 7,040,313 B2 | 5/2006 | Fine et al. |
| 7,122,018 B2 | 10/2006 | Stenzler et al. |
| 7,220,393 B2 | 5/2007 | Miller et al. |
| 7,255,105 B2 | 8/2007 | Figley et al. |
| 7,335,181 B2 | 2/2008 | Miller et al. |
| 7,485,324 B2 | 2/2009 | Miller et al. |
| 7,498,000 B2 | 3/2009 | Pekshev et al. |
| 7,516,742 B2 | 4/2009 | Stenzler et al. |
| 7,520,866 B2 | 4/2009 | Stenzler et al. |
| 7,531,133 B2 | 5/2009 | Hole et al. |
| 7,560,076 B2 | 7/2009 | Rounbehler et al. |
| 7,589,473 B2 | 9/2009 | Suslov |
| 7,744,812 B2 | 6/2010 | Witherspoon et al. |
| 7,861,717 B1 | 1/2011 | Krebs |
| 7,955,294 B2 | 6/2011 | Stenzler et al. |
| 8,030,849 B2 | 10/2011 | Suslov |
| 8,043,252 B2 | 10/2011 | Miller et al. |
| 8,079,998 B2 | 12/2011 | Hole et al. |
| 8,151,791 B2 | 4/2012 | Arlow et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,344,627 B1 | 1/2013 | Hooke et al. |
| 8,431,163 B2 | 4/2013 | Baldassarre et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,717,733 B2 | 5/2014 | Gefter et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,821,828 B2 | 9/2014 | Hilbig et al. |
| 8,846,112 B2 | 9/2014 | Baldassarre |
| 9,095,534 B2 | 8/2015 | Stenzler et al. |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,408,993 B2 | 8/2016 | Bathe et al. |
| 9,573,110 B2 | 2/2017 | Montgomery et al. |
| 9,770,570 B2 | 9/2017 | Schnitman et al. |
| 9,982,354 B2 | 5/2018 | Kim |
| 2001/0031230 A1 | 10/2001 | Castor et al. |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsey |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0281465 A1 | 12/2005 | Marquart et al. |
| 2006/0025700 A1 | 2/2006 | Fallik |
| 2006/0172018 A1 | 8/2006 | Fine et al. |
| 2006/0276844 A1 | 12/2006 | Alon et al. |
| 2007/0151561 A1 | 7/2007 | Laurila |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |

(56) References Cited

U.S. PATENT DOCUMENTS

| | | |
|---|---|---|
| 2008/0202509 A1 | 8/2008 | Dillon et al. |
| 2010/0189808 A1 | 7/2010 | Gupta et al. |
| 2010/0275911 A1 | 11/2010 | Arlow et al. |
| 2012/0279500 A1 | 11/2012 | Singvogel et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2014/0031668 A1 | 1/2014 | Mobasser et al. |
| 2014/0158121 A1 | 6/2014 | Flanagan et al. |
| 2014/0251787 A1* | 9/2014 | Montgomery .......... C01B 21/32 204/179 |
| 2014/0363525 A1 | 12/2014 | Montgomery et al. |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0090261 A1 | 4/2015 | Crosbie |
| 2015/0174158 A1 | 6/2015 | Av-Gay et al. |
| 2015/0272988 A1 | 10/2015 | Av-Gay et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0243328 A1 | 8/2016 | Tolmie et al. |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2018/0125883 A1 | 5/2018 | Av-Gay et al. |
| 2018/0133246 A1 | 5/2018 | Av-Gay et al. |

FOREIGN PATENT DOCUMENTS

| | | |
|---|---|---|
| CN | 101828432 A | 9/2010 |
| EP | 0621051 A2 | 10/1994 |
| EP | 1036758 A1 | 9/2000 |
| EP | 1854494 A1 | 11/2007 |
| EP | 2151554 A1 | 2/2010 |
| JP | H04132560 A | 5/1992 |
| JP | 2000102616 A | 4/2000 |
| JP | 2001517108 A | 10/2001 |
| JP | 2006273677 A | 10/2006 |
| WO | 2004032719 A2 | 4/2004 |
| WO | 2011002606 A1 | 1/2011 |
| WO | 2012094008 A1 | 7/2012 |
| WO | 2013052548 A2 | 4/2013 |
| WO | 2013070712 A1 | 5/2013 |
| WO | 2013181179 A1 | 12/2013 |
| WO | 2014085719 A1 | 6/2014 |
| WO | 2014143842 A1 | 9/2014 |
| WO | 2014144151 A1 | 9/2014 |
| WO | 2015066278 A1 | 5/2015 |
| WO | 2015127085 A1 | 8/2015 |

OTHER PUBLICATIONS

Keshav, Using Plasmas for High-Speed Flow Control and Combustion Control, Dissertation for Degree of Doctor of Philosophy, The Ohio State University, 2008, 268 pages.

Namihira, et al., Production of Nitric Oxide Using a Pulsed Arc Discharge, IEEE Transactions on Plasma Science, 2002, 30(5):1993-1998.

PCT International Search Report, PCT/US2014/028439, dated Jul. 24, 2014.

PCT International Preliminary Report on Patentability, PCT/US2014/028439, dated Sep. 15, 2015.

PCT International Search Report, PCT/US2014/027986, dated Jul. 17, 2014.

PCT International Preliminary Report on Patentability, PCT/US2014/027986, dated Sep. 15, 2015.

PCT International Search Report and Written Opinion, PCT/US2015/056443, dated Jan. 6, 2016.

\* cited by examiner

SYNTHESIS OF NITRIC OXIDE GAS FOR INHALATION

CLAIM OF PRIORITY

Cross-Reference to Related Applications

This application is a continuation of U.S. patent application Ser. No. 14/777,084 which represents the national stage entry of PCT International Application No. PCT/US2014/027986 filed Mar. 14, 2014, which claims priority to U.S. Patent Application Ser. No. 61/789,161 filed Mar. 15, 2013, and U.S. Provisional Application Ser. No. 61/792,473, filed Mar. 15, 2013, which are hereby incorporated by reference in their entirety for all purposes.

TECHNICAL FIELD

This invention is related to synthesis of nitric oxide gas for inhalation.

BACKGROUND

Nitric oxide (NO) is a crucial mediator of many biological systems, and is known to mediate the control of systemic and pulmonary artery blood pressure, help the immune system kill invading parasites that enter cells, inhibit the division of cancer cells, transmit signals between brain cells, and contribute to the death of brain cells that can debilitate people with strokes or heart attacks. Nitric oxide also mediates the relaxation of smooth muscle present, for example, in the walls of blood vessels, bronchi, the gastrointestinal tract, and urogenital tract. Administration of nitric oxide gas to the lung by inhalation has been shown to produce localized smooth muscle relaxation to treat pulmonary hypertension, pneumonia, hypoxemic respiratory failure of the newborn, etc. without producing systemic side effects.

Inhaled nitric oxide is a potent local pulmonary vasodilator that improves the matching of ventilation with perfusion, thereby increasing the injured lungs oxygen transport efficiency, and raises the arterial oxygen tension. Breathing nitric oxide combines a rapid onset of action occurring within seconds with the absence of systemic vasodilation. Once inhaled, NO diffuses through the pulmonary vasculature into the bloodstream, where it is rapidly inactivated by combination with hemoglobin. Therefore, the vasodilatory effects of inhaled nitric oxide are limited to the pulmonary vasculature. The ability of nitric oxide to dilate pulmonary vessels selectively provides therapeutic advantages in the treatment of acute and chronic pulmonary hypertension. Inhaled NO has also been used to prevent ischemia reperfusion injury after PCI in adults with heart attacks. Inhaled NO can produce systemic anti-inflammatory and anti-platelet effects by increasing the levels of circulating NO bio-metabolites and other mechanisms.

U.S. Pat. No. 5,396,882 to Zapol, which is incorporated by reference herein, describes electric generation of nitric oxide (NO) from air at ambient pressure for medical purposes. As described in U.S. Pat. No. 5,396,882, an air input port of the system is used for continuously introducing air into the region of the electric arc.

SUMMARY

In some aspects, a method includes collecting information related to one or more conditions of a respiratory system associated with a patient. The method also includes determining one or more control parameters based on the collected information. The method also includes initiating a series of electric arcs external to the patient to generate nitric oxide based on the determined control parameters.

Embodiments can include one or more of the following.

The conditions associated with the respiratory system can include one or more of the oxygen concentration of a reactant gas a flow rate of the reactant gas, a volume and timing of an inspiration, the oxygen concentration of a product gas, the nitric oxide concentration of the product gas, the nitrogen dioxide concentration of the product gas, the ozone concentration of the product gas, the nitric oxide concentration of an inhaled gas, and the nitrogen dioxide concentration of the inhaled gas.

The volume and timing of an inspiration can be received from a ventilator.

A pulse train can initiate the series of electric arcs, and the pulse train can include pulse groups having pulses with different pulse widths.

The pulse width of initial pulses in one of the pulse groups can be wider than other pulses in the pulse group.

The series of electric arcs can generate a reduced level of nitrogen dioxide.

The series of electric arcs can generate a reduced level of ozone.

The reduced level of nitrogen dioxide can be further reduced by a scavenger including one or more of KaOH, CaOH, CaCO3, and NaOH.

The reduced level of nitrogen dioxide, can have a concentration that is less than 20%, 10%, 6%, or 5% of a concentration of the generated nitric oxide.

The series of electric arcs can be generated by electrodes including a noble metal.

The series of electric arcs can be generated by electrodes including iridium.

The series of electric arcs can be generated by electrodes including nickel.

In some additional aspects, an apparatus includes a chamber having an inlet valve for receiving a reactant gas and an outlet valve for delivering a product gas. The apparatus also includes a sensor for collecting information related to one or more conditions of a respiratory system associated with a patient. The apparatus also includes a controller for determining one or more control parameters based on the collected information. One or more pairs of electrodes are included in the apparatus and positioned inside the chamber for initiating a series of electric arcs external to the patient to generate nitric oxide based on the determined control parameters.

Embodiments can include one or more of the following.

The conditions associated with the respiratory system can include one or more of the oxygen concentration of the reactant gas, a flow rate of the reactant gas, a volume and timing of an inspiration, the oxygen concentration of the product gas, the nitric oxide concentration of the product gas, the nitrogen dioxide concentration of the product gas, the ozone concentration of the product gas, the nitric oxide concentration of an inhaled gas, the nitrogen dioxide concentration of the inhaled gas, and the pressure in the chamber.

The volume and timing of an inspiration can be received from a ventilator.

A pulse train can initiate the series of electric arcs, and the pulse train can include pulse groups having pulses with different pulse widths.

The pulse width of initial pulses in one of the pulse groups can be wider than other pulses in the pulse group.

The series of electric arcs can generate a reduced level of nitrogen dioxide.

The series of electric arcs can generate a reduced level of ozone.

The series of electric arcs can be initiated when the chamber has a pressure greater than 1 ATA or less than 1 ATA.

The apparatus can also include a scavenger for further reducing the reduced level of nitrogen dioxide, and the scavenger can include one or more of KaOH, CaOH, CaCO3, and NaOH.

The reduced level of nitrogen dioxide can have a concentration that is less than 20%, 10%, 6%, or 5% of a concentration of the generated nitric oxide.

The electrodes can include a noble metal.

The electrodes can include iridium.

The electrodes can include nickel.

In some additional aspects, an apparatus includes a chamber having an inlet valve for receiving a reactant gas and an outlet valve for delivering a product gas. The apparatus also includes a piston positioned inside the chamber and configured to move along a length of the chamber for adjusting pressure in the chamber. The apparatus also includes a sensor for collecting information related to one or more conditions of a respiratory system associated with a patient. The apparatus includes a controller for determining one or more control parameters based on the collected information. One or more pairs of electrodes are included and positioned inside the chamber for initiating a series of electric arcs external to the patient to generate nitric oxide based on the determined control parameters.

Embodiments can include one or more of the following.

The conditions associated with the respiratory system can include one or more of the oxygen concentration of the reactant gas, a flow rate of the reactant gas, a volume and timing of an inspiration, the oxygen concentration of the product gas, the nitric oxide concentration of the product gas, the nitrogen dioxide concentration of the product gas, the ozone concentration of the product gas, the nitric oxide concentration of an inhaled gas, the nitrogen dioxide concentration of the inhaled gas, and the pressure in the chamber.

The volume and timing of an inspiration can be received from a ventilator.

A pulse train can initiate the series of electric arcs, and the pulse train can include pulse groups having pulses with different pulse widths.

The pulse width of initial pulses in one of the pulse groups can be wider than other pulses in the pulse group.

The series of electric arcs can generate a reduced level of nitrogen dioxide.

The series of electric arcs can generate a reduced level of ozone.

The series of electric arcs can be initiated when the chamber has a pressure greater than 1 ATA or less than 1 ATA.

The apparatus can also include a scavenger for further reducing the reduced level to of nitrogen dioxide, and the scavenger can include one or more of KaOH, CaOH, CaCO3, and NaOH.

The reduced level of nitrogen dioxide can have a concentration that is less than 20%, 10%, 6%, or 5% of a concentration of the generated nitric oxide.

The electrodes can include a noble metal.

The electrodes can include iridium.

The electrodes can include nickel.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Synthesis of NO for inhalation is achieved by electrically sparking a reactant gas including $N_2$ and $O_2$ (e.g., air), thereby forming a product gas including the electrically synthesized NO. The synthesis may be achieved under hypobaric or hyperbaric conditions. As used herein, "hypobaric" generally refers to a pressure less than 1 ATA (atmosphere absolute), and "hyperbaric" to a pressure greater than 1 ATA. The product gas can include a medically acceptable level of $NO_2$ (e.g., usually less than 5 ppm, and sometimes less than 1-2 ppm). The product gas may be inhaled either with or without reducing the concentration of $NO_2$ in the product gas. Apparatuses described herein for synthesis of nitric oxide can be portable, light-weight, self-powered, and can be used to provide product gas for therapeutic use, with a concentration of NO in the range of 0.5 ppm to 500 ppm and a concentration of $NO_2$ of less than 1% of the NO concentration, or even lower (e.g., less than 1%) after using a scavenger.

Figure 1:
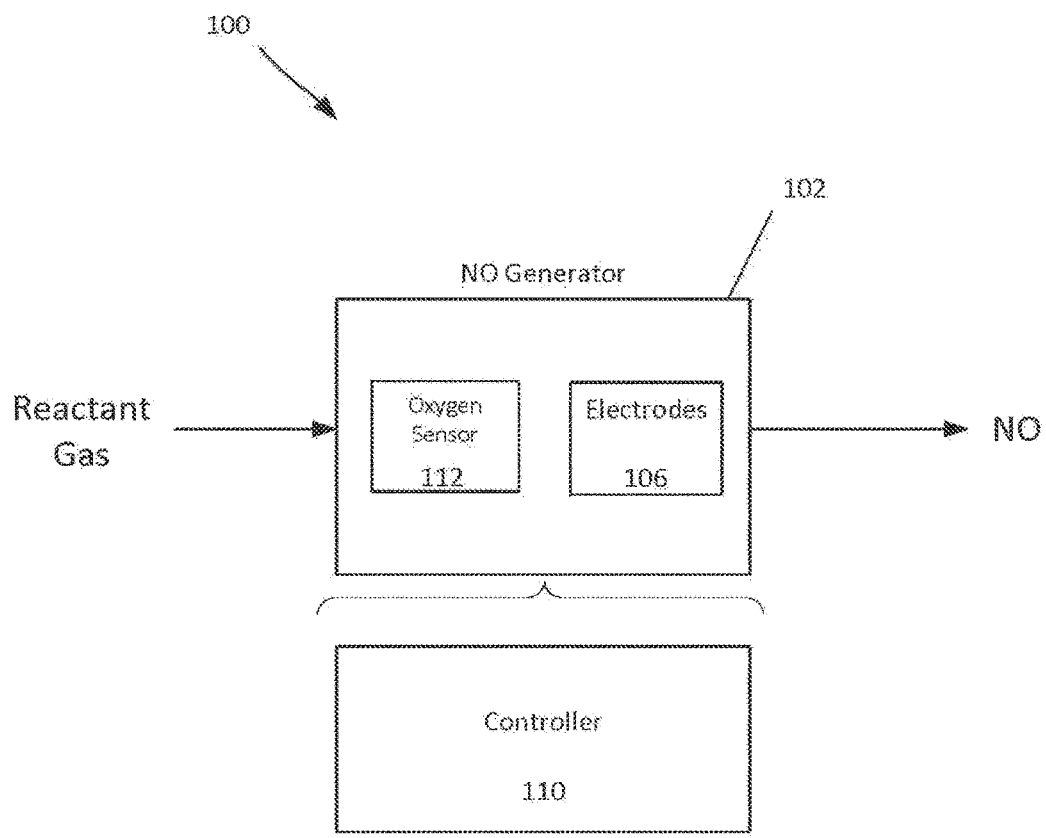
FIG. 1 is a block diagram of a respiratory system for producing NO.

FIG. 1 shows an example of a respiratory system 100 for producing NO. A reactant gas (e.g., air, or a 10-90% oxygen mixture in nitrogen) enters an NO generator 102, and a product gas (including NO) exits the NO generator 102. The NO generator 102 includes electrodes 106 and a controller 110. If the reactant gas is a gas other than air, the NO generator 102 can include an oxygen level sensor 112. NO production is proportional to oxygen and nitrogen concentration and maximal at about 50% oxygen at atmospheric pressure (1 ATA). The oxygen level sensor 112 can be an electrode configured to detect a concentration of oxygen in the reactant gas, as described in more detail below. The electrodes 106 generate sparks in the presence of the reactant gas to produce NO 104, as described herein.

Figure 2:
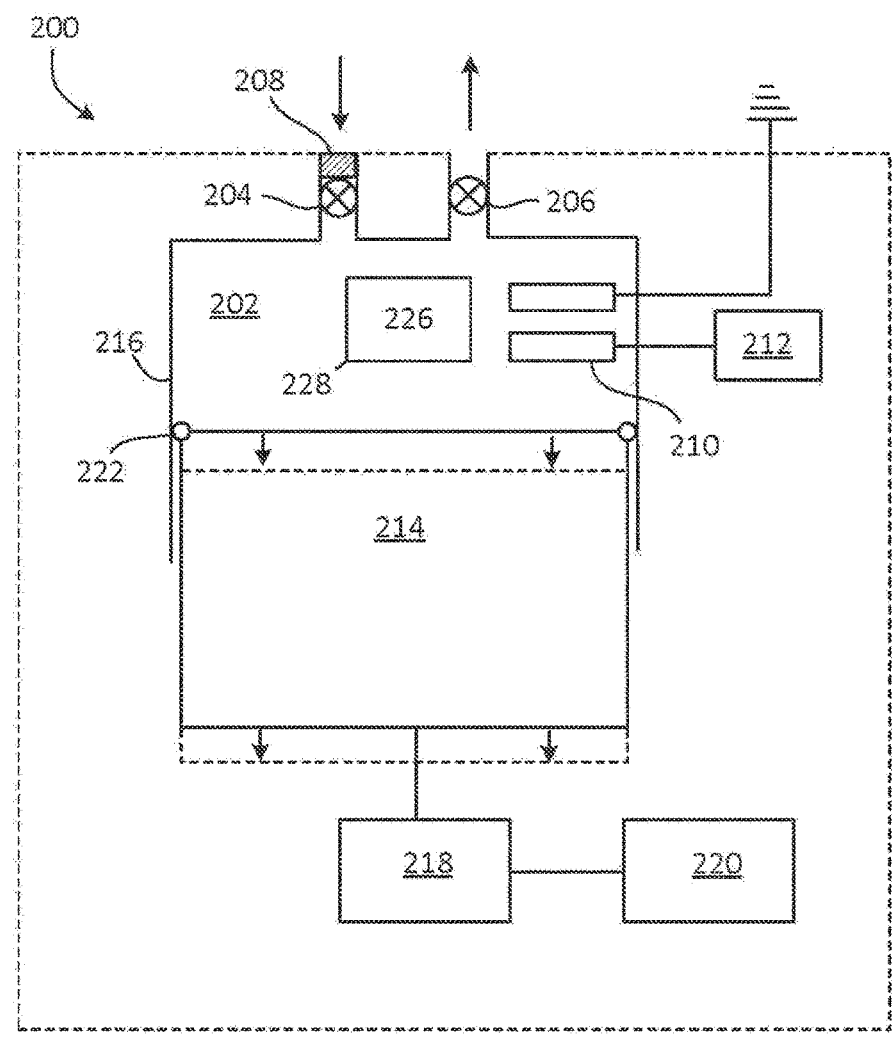
FIG. 2 is an example of an NO generator.

FIG. 2 shows an example of an NO generator 200. NO generator 200 includes chamber 202 having inlet valve 204 and outlet valve 206. In some cases, filter 208 is coupled to NO generator 200, such that a gaseous mixture including $N_2$ and $O_2$ entering chamber through inlet valve 204 is filtered to remove particulate matter (e.g., dust) or water vapor. Chamber 202 includes electrodes 210. Electrodes 210 are separated by a gap, and one of the electrodes is coupled to voltage source 212. Voltage source 212 is suitable to create a spark or corona discharge capable of forming NO from $N_2$ and $O_2$ between electrodes 210. Examples of voltage source 212 include, but are not limited to, a piezoelectric crystal, a battery (e.g., a motorcycle battery), a solar cell, a wind generator, or other source suitable to produce a current on the order of nanoamperes or milliamperes and a voltage of 1 to 25 kV (e.g., a power of 1 to 100 watts), or a voltage of 1 to 10 kV or 1 to 5 kV.

When NO generator 200 is used for hypobaric or hyperbaric synthesis of NO, chamber 202 may be a cavity in a positive displacement pump. As shown in FIG. 2, chamber 202 may be a cavity in a piston pump and has a variable volume defined by the position of piston 214 in barrel 216. Piston 214 is coupled to actuator 218. In one example, actuator 218 includes an eccentric mechanism driven by a rod or shaft.

Actuator 218 is driven by prime mover 120 in a reciprocating manner. Prime mover 220 may be, for example, a motor or engine (e.g., an electric or gasoline or diesel powered engine) arranged to translate piston 214 with respect to barrel 216 by way of actuator 218. Seal 222 inhibits the flow of air into or out of chamber 202 between piston 214 and barrel 216. Thus, when both inlet valve 204 and outlet valve 206 are closed, translation of piston 214 away from electrodes 210 by actuator 218 increases the volume of chamber 202, thereby reducing the pressure in chamber 202 to a pressure below atmospheric pressure and reducing a concentration of gases (e.g., $N_2$ and $O_2$) in a reactant gas present in the chamber. Conversely, translation of piston 214 toward the electrodes 210 by actuator 218 decreases the volume of chamber 202, thereby increasing the pressure in chamber 202 to a pressure above atmospheric pressure and increasing the pressure and concentration of gases in a reactant gas present in the chamber. Because NO production is proportional to oxygen concentration, the pressure of the chamber 202 can have an effect on the production of NO. For example, when the chamber 202 has a relatively high pressure (e.g., 2 ATA), NO production is increased.

Inlet valve 204 may be exposed to the environment such that, with the inlet valve open, ambient air (or other reactant gas containing $N_2$ and $O_2$) enters chamber 202. With air in chamber 202, inlet valve is closed and piston 214 translates away from electrodes 210, thereby increasing the volume of chamber 202 and decreasing the pressure inside chamber 202 to a pressure below atmospheric pressure. As the volume of chamber 202 increases, the concentration of $O_2$ in the chamber falls below the concentration of $O_2$ in air at atmospheric pressure (e.g., falls below 21 vol %). Actuator 218 may be controlled to increase a volume of chamber 202 by a factor of 2, 3, 4, etc., thereby reducing a pressure in chamber 202 to a fraction (e.g., ½, ⅓, ¼, etc.) of atmospheric pressure. While the pressure in chamber 202 is below atmospheric pressure, voltage source 212 initiates sparks or corona discharges across electrodes 210, thereby electrically generating NO. Following the sparks or corona discharges, actuator 218 continues its reciprocating cycle, and outlet valve 206 is opened to release the product gas containing the electrically generated NO. Thus, inlet valve 204 and outlet valve 206 operate out of phase with each other, such that outlet valve 206 is closed when inlet valve 104 is open, and inlet valve 204 is closed when outlet valve 206 is open.

Conversely, with air in chamber 202, inlet valve is closed and piston 214 translates toward the electrodes 210, thereby decreasing the volume of chamber 202 and increasing the pressure inside chamber 202 to a pressure above atmospheric pressure. As the volume of chamber 202 decreases, the pressure (concentration) of $O_2$ in the chamber rises above the pressure (concentration) of $O_2$ in air at atmospheric pressure (e.g., rises above 21 vol %). Actuator 218 may be controlled to decrease a volume of chamber 202 to a fraction of ½, ⅓, ¼, etc., thereby increasing a pressure in chamber 202 to 2, 3, 4, etc. times atmospheric pressure. While the pressure in chamber 202 is above atmospheric pressure, voltage source 212 initiates sparks or corona discharges across electrodes 210, thereby electrically generating NO.

Figure 13:
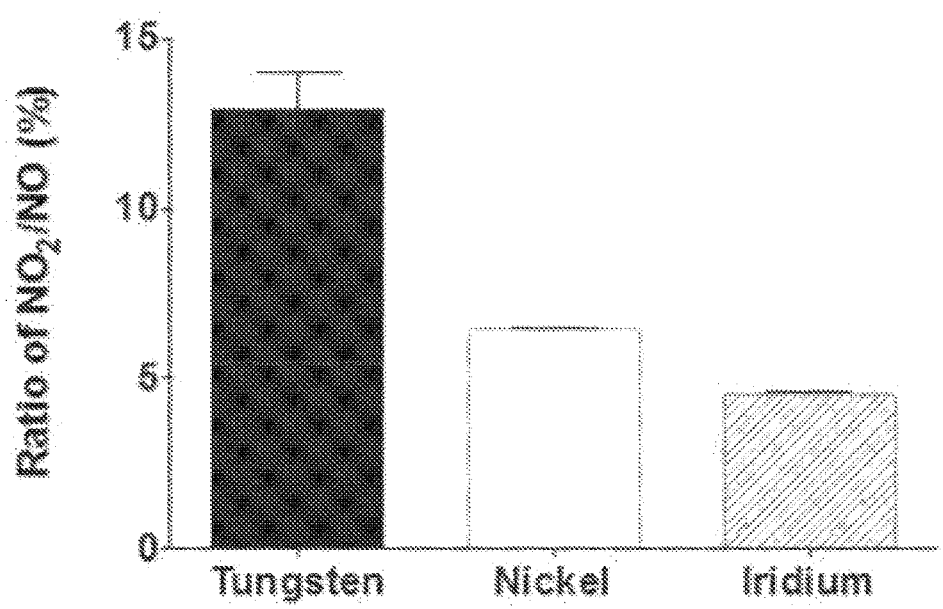
FIG. 13 shows NO and $NO_2$ concentrations using various electrode materials.

In some examples, electrodes in an NO generator (e.g., electrodes 210) can be duplicated for safety purposes to provide a spare. The electrodes 210 can be doubled or tripled for increased power and NO production with large tidal volumes. Referring briefly to FIG. 13, the electrodes 210 can contain iridium, tungsten, stainless steel, or nickel, to name a few. In some examples, electrodes 210 that contain a noble metal (e.g., iridium) produce the smallest ratio of $NO_2$/NO.

Figure 3:
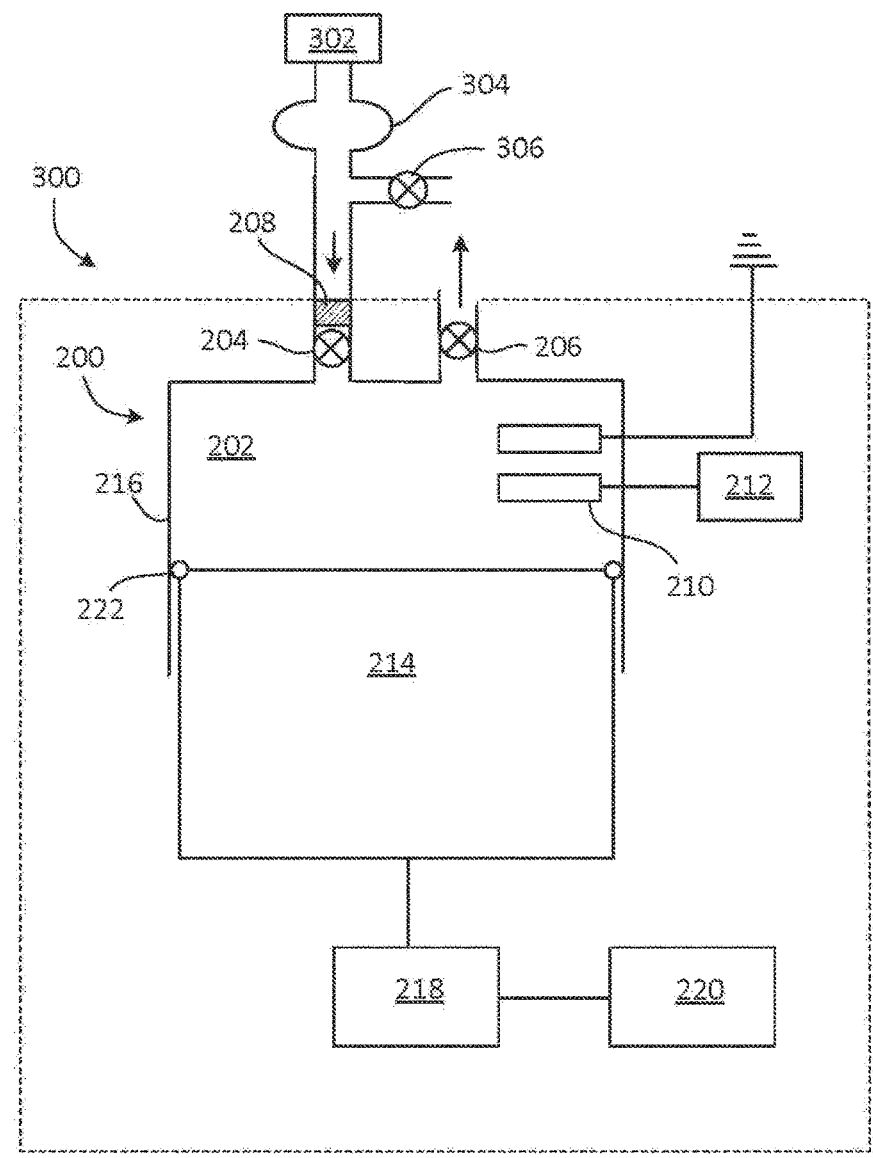
FIG. 3 is an example of an NO generator.

FIG. 3 shows an example of an NO generator 300. NO generator 300 includes components of NO generator 200, as described with respect to FIG. 2, with source 302 coupled to inlet valve 204 and arranged to provide a reactant gas to chamber 202. In some instances, source 302 is an apparatus arranged to provide a reactant gas with a concentration of $O_2$ less than 21 vol % or less than 20 vol %. In some instances, source 302 is an apparatus arranged to provide a reactant gas with a concentration of $O_2$ more than 21 vol % but not more than 90 vol %. For example, source 302 may include a cylinder of $N_2$ or an inert gas (e.g., argon or helium) and a mechanism to mix the $N_2$ or inert gas with air or an enriched oxygen containing source at a selected ratio to achieve a desired concentration of $O_2$, $N_2$, and/or other components in the reactant gas provided to chamber 202. In some examples, an oxygen cylinder, an oxygen concentration, or an oxygen generator is used to raise the concentration of oxygen in the reactant gas. The reactant gas is typically provided to chamber 202 at a pressure of 1 ATA (atmosphere absolute) or above (e.g., slightly above, to 3 ATA) to avoid admixture of the reactant gas with air. Before entering chamber 202, reactant gas from source 302 may pass through an equilibrium bag 304, held slightly above atmospheric pressure. Blow-off valve 306 may be present to allow the pressure of the reactant gas to be maintained close to atmospheric pressure.

Figure 4:
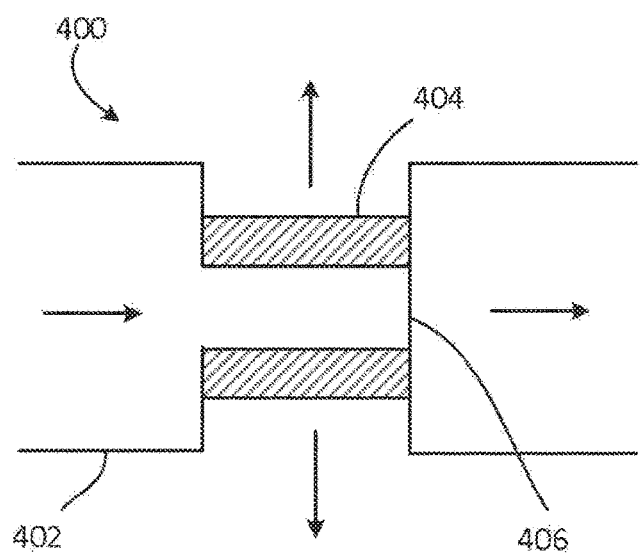
FIG. 4 depicts a device for concentrating oxygen.

In some instances, source 302 includes an oxygen concentrator, oxygen generator, or oxygen cylinder. FIG. 4 depicts an oxygen concentrator 400, in which pressurized air enters oxygen concentrator 400 through inlet 402 and passes through molecular sieve 404, yielding oxygen-enriched gas (e.g., having at least 30 vol % or 50 vol % $O_2$). The exhaust gas, which has an $O_2$ concentration less than that of ambient air and a $N_2$ concentration greater than that of ambient air, exits oxygen concentrator 400 through valve 406, and is provided to the inlet valve 204.

Figure 5:
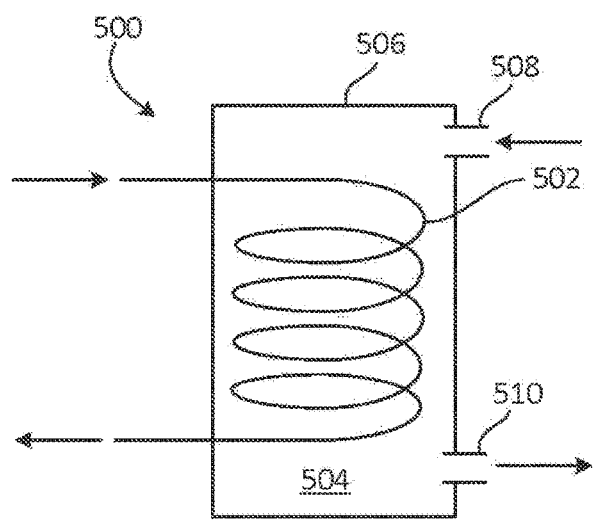
FIG. 5 depicts a device for cooling a gas.

In some instances, source 302 includes an apparatus for cooling air (e.g., a copper tube heat exchanger), such that air at a temperature less than room temperature (e.g., a temperature approaching 0° K) is provided to chamber 202 through valve 204, and the spark or corona discharge occurs in a cooled reactant gas having a temperature less than room temperature. Source 302 may operate to cool air by refrigeration or heat exchange methods generally known in the art. FIG. 5 depicts one example of a cooling device 500, in which air or another reactant gas (e.g., a mixture of air and $N_2$ or an inert gas, such as argon, helium, or the like) flows through coil 502 and is cooled by coolant 504, which enters chamber 506 through inlet 508 and exits the chamber through outlet 510. Coil 502 may be a heat-conductive tubing such as, for example, copper tubing. Coolant 504 may be, for example, liquid $N_2$ or a cycling refrigerant (e.g., chlorofluorocarbon or hydrochlorofluorocarbon).

In certain instances, one or more implementations of source 302 as described above with respect to FIG. 3 are combined to form a gaseous mixture. For example, source 302 may include a cylinder of $N_2$ or an inert gas (e.g., argon or helium) and a mechanism to mix the $N_2$ or inert gas with air at a selected ratio to achieve a desired concentration of $O_2$ as measured, for example, with a sensor including an electrode, as well as an apparatus to cool the reactant gas before the reactant gas is provided to chamber 202. An apparatus to cool the reactant gas may cool the reactant gas at more than one location (e.g., at the regulator or cylinder head of a gas cylinder, at valve 204, and the like).

Figure 6:
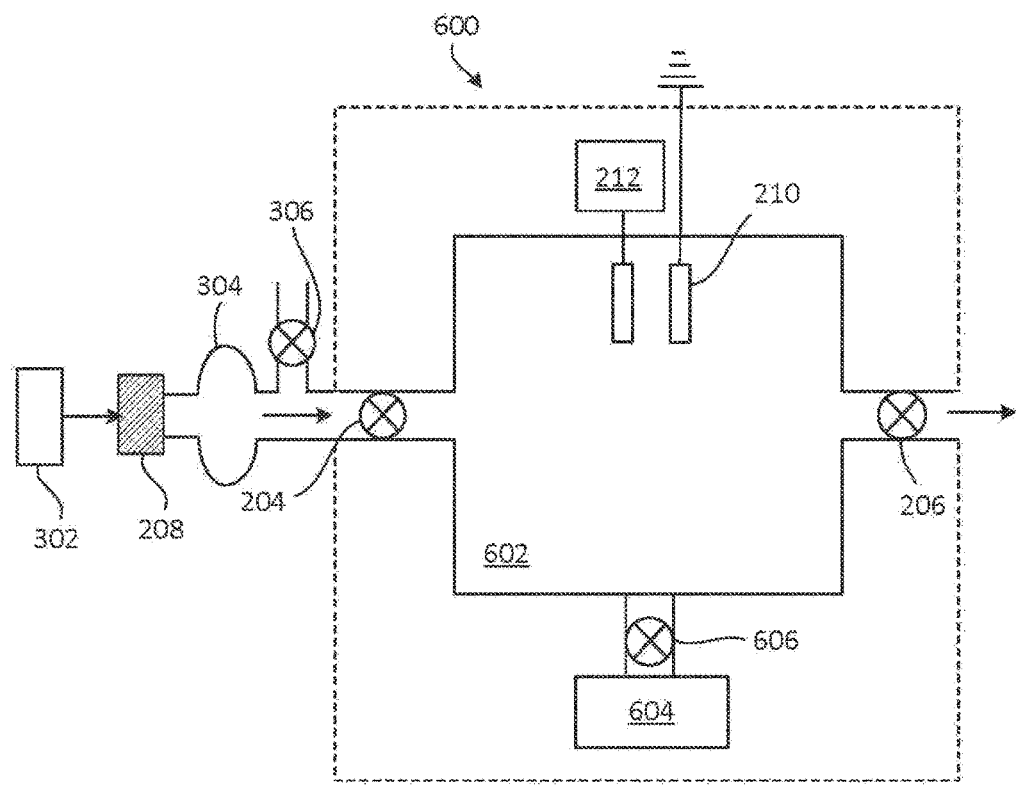
FIG. 6 is an example of an NO generator.

In other embodiments, as shown in FIG. 6, an NO generator 600 includes constant volume chamber 602. In some cases, inlet valve 204 is exposed to the environment such that, with the inlet valve open, ambient air enters chamber 602 (e.g., through filter 208). Inlet valve 204 and outlet valve 206 may be synchronized such that a gaseous mixture flows into chamber 602 through inlet valve 204, and the inlet valve is closed before the sparks or corona discharges are initiated. Outlet valve 206 is typically closed while inlet valve 204 is open, and may open prior to, during, or after initiation of the sparks or corona discharges. In certain cases, constant volume chamber 602 is coupled to source 302, and reactant gas is provided to chamber 602 by source 302. Filter 208 may be positioned between source 302 and chamber 602 (e.g., between source 302 and equilibrium bag 304, as illustrated, or between blow-off valve 306 and inlet valve 204, as shown in FIG. 3). The exhaust of an oxygen concentrator may be used to provide a reactant gas having a decreased $O_2$ content to chamber 602. NO generator 600 may be operated in an environment having an ambient pressure less than 1 ATA (e.g., at high altitude). Alternatively, constant volume 602 chamber is coupled to pump 604 through valve 606. Pump 604 may be, for example, a positive displacement pump such as a lobe pump or a vane pump, arranged to decrease the gas pressure in chamber 602, thereby decreasing the concentration of $O_2$ and $N_2$ in the reactant gas in chamber 602. Similarly, pump 604 can be arranged to increase the gas pressure in chamber 602, thereby increasing the concentration of $O_2$ and $N_2$ in the reactant gas in chamber 602 to achieve higher levels of NO generation.

Figure 7:
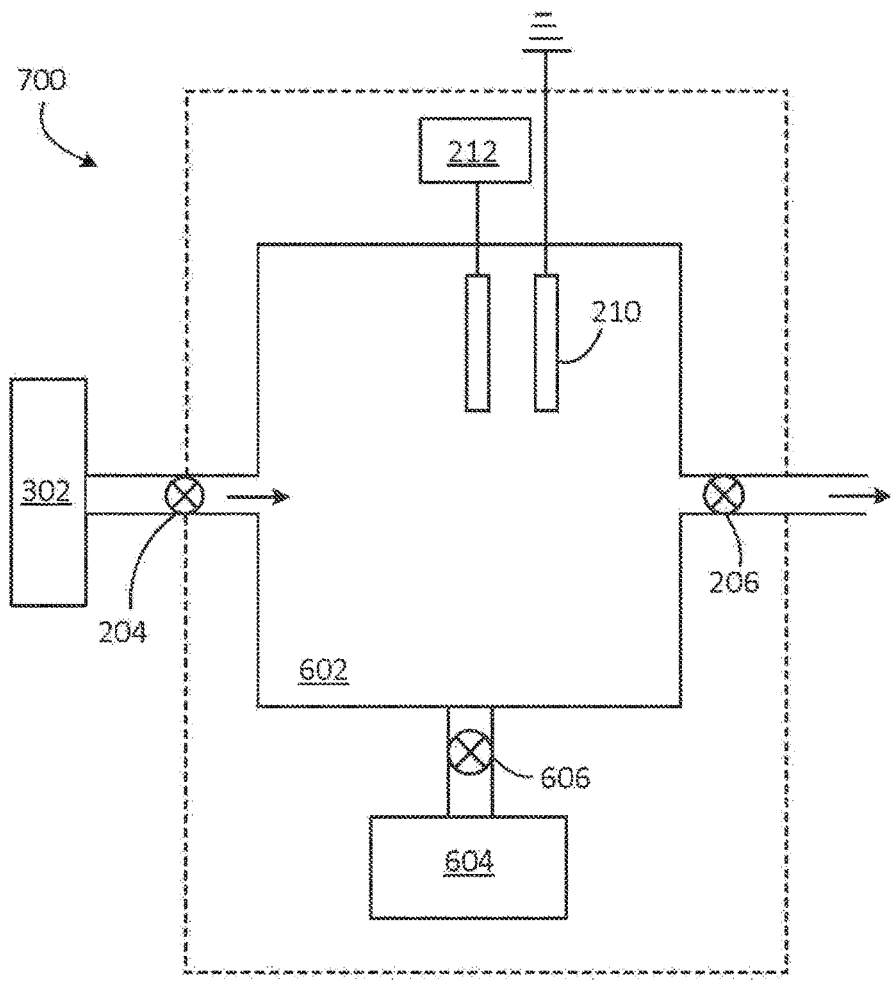
FIG. 7 is an example of an NO generator.

FIG. 7 shows an example of an NO generator 700. NO generator 700 includes components of NO generator 500, as described with respect to FIG. 6, with source 302, as described with respect to FIG. 3, coupled to inlet valve 204 and arranged to provide a reactant gas to chamber 602. As noted with respect to FIG. 6, NO may be selectively synthesized in chamber 602 at ambient pressure, at a reduced pressure, or at an increased to pressure achieved with pump 604.

The product gas that exits chamber 202 or 602 through outlet valve 206 of NO generator 200, 300, 600, and 700 includes the electrically generated NO, and may include low levels of $NO_2$ and $O_3$. In some cases, the product or effluent gas can be gauged to a piston to raise the pressure of the produced gas for injection into a ventilator, or coupled to an endotracheal tube for continuous injection or injection coupled with inspiration and proportional to airway flow. The product gas can be stored briefly at atmospheric pressure (e.g., stored for seconds before direct inhalation by a patient through a mask, before injection into an airstream for ventilation, or before use thereof to drive a ventilator). The product gas can be admixed in ventilator gases. In certain cases, the product gas may be treated to reduce a concentration of one or more components in the gas. In one example, the product gas is combined with ambient or pressurized air or oxygen to yield a lower effective concentration of NO. In some examples, the product gas is treated to remove one or more unwanted by-products (e.g., $NO_2$ and $O_3$) by contacting the product gas with a scavenger (e.g., scavenger 226). In some examples, the scavenger 226 includes one or more of KaOH, CaOH, $CaCO_3$, and NaOH.

Referring to FIG. 2, the scavenger 226 can be placed in a cartridge 228 to process produced gas exiting the outlet valve 206. The cartridge 228, the scavenger 226, or both may be replaceable due to the limited absorption capabilities of the scavenger material. The scavenger 226 can indicate its extent of absorption (i.e., how close the scavenger is to maximum absorption) by changing color. In some examples, at a concentration of 80 ppm NO in the product gas, a scavenger 226 having a volume of 100 ml can reduce the concentration of $NO_2$ to about 0 ppm.

In certain cases, including implementations of NO generator 300 and 700 in which exhaust gas from an oxygen concentrator is used for hypobaric synthesis of NO, the product gas that exits chamber 202 or 602 through outlet valve 206 may be combined with $O_2$-enriched air from the oxygen concentrator or pure $O_2$ from a source to form a gaseous mixture including a medically effective level of NO in $O_2$-enriched air, with low levels of $NO_2$. One or more methods of treating the product gas can be combined in any order such that, for example, $NO_2$ is removed from a product gas that exits chamber 202 or 602 through outlet valve 206 to yield a gaseous mixture, and this gaseous mixture is then combined with $O_2$-enriched air from an oxygen concentrator, or a product gas that exits chamber 202 or 602 through outlet valve 206 is combined with $O_2$-enriched air from an oxygen concentrator to form a gaseous mixture, and $NO_2$ is then removed from the gaseous mixture. The final mixture can be again subjected to scavenging to remove $NO_2$.

In some instances, the concentration of one or more components in the product gas can be adjusted by varying the flow of gas through the inlet valve, varying the spark or discharge frequency, varying the voltage or current supplied to the electrodes, as described in more detail below, or adding multiple series of sparking electrodes.

Figure 8:
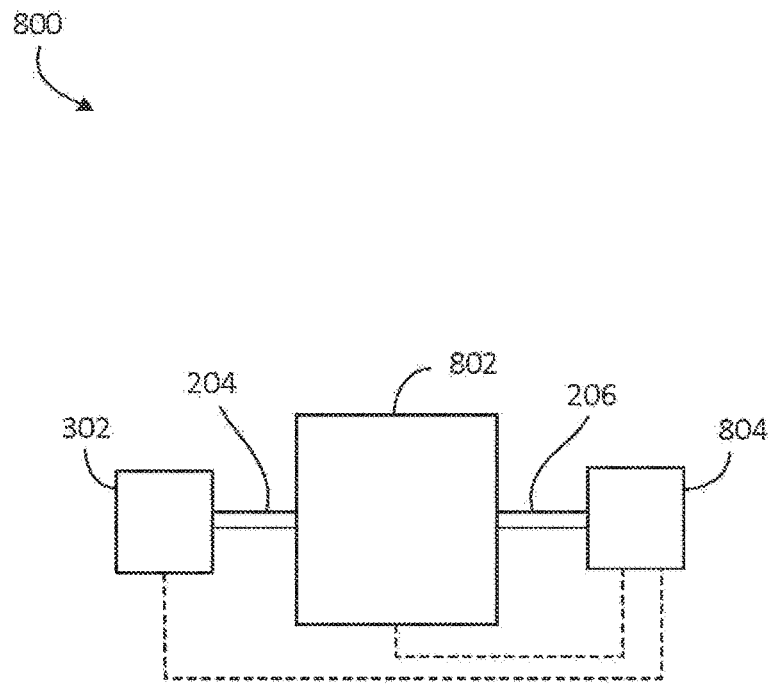
FIG. 8 is an example of an NO generator.

FIG. 8 depicts a respiratory system 800 for electric synthesis of NO in which product gas from output valve 206 of NO generator 802 is provided to monitor 804. The monitor 804 can collect information related to one or more conditions associated with the respiratory system. NO generator 802 may be any NO generator described herein. Monitor 804 may include one or more sensors for assessing a concentration of one or more components in the product gas. In some examples, the sensors use electrodes, chemiluminescent, or UV absorption means to measure the concentration of NO, $NO_2$, $O_3$, $O_2$, or any combination thereof. In some cases, monitor 804 provides feedback to NO generator 802 or source 302 to adjust production of NO, decrease production of $NO_2$ or $O_3$, etc. For instance, an assessed concentration of NO is used to adjust the flow or concentration of reactant gas or a gas to be mixed with the reactant gas (e.g., $N_2$, an inert gas, air, or $O_2$) into the chamber (e.g., chamber 202 or 602), the electrode size, spacing, or temperature, the spark frequency, or voltage, peak current, or limiting current of an NO generator. In one example, if an assessed concentration of NO is higher than desired, the flow of gas into the chamber can be increased accordingly, thereby reducing the concentration of NO in the product gas. In some examples, a gas pump causes the gas to flow into the chamber. The monitor 804 can include a gas flow sensor for measuring the flow rate of the gas entering the chamber.

As described herein, an NO generator produces gas for respiration with a concentration of NO between 0.5 ppm and 500 ppm (e.g., at least 0.5 ppm and up to 1 ppm, 5 ppm, 10 ppm, 20 ppm, 40 ppm, 80 ppm, or 500 ppm). The produced gas may be diluted before inhalation. The gas can be used to oxidize hemoglobin ex vivo (e.g., in a stored blood transfusion) or inhaled by adults, children, or newborns to therapeutically treat respiratory disorders by selective pulmonary vasodilation, including pulmonary fibrosis, infection, malaria, myocardial infarction, stroke, pulmonary hypertension, persistent pulmonary hypertension newborns, and other conditions in which breathing NO to oxidize hemoglobin or to deliver NO metabolites into the circulation is valuable. In some cases, the NO generator can be used to supply gas for breathing to humans experiencing pulmonary hypertension and hypoxia as a result of explosive decompression of an aircraft or spacecraft, to treat high altitude pulmonary edema, and/or to treat any medical condition at high altitude by sparking or corona discharge of air in a hypobaric environment, with advantages including rapid, hypobaric synthesis of a breathable therapeutic gas including NO in the absence of gas cylinders.

In some embodiments, for example when an NO generator is used to provide input to a ventilator, the operation of the NO generator (e.g., the timing and frequency of the spark or corona discharge, the opening and closing of the inlet valve and the outlet valve, and the like) is synchronized with the inspiratory pressurization or gas flow in the airway (e.g., as measured by a hot wire anemometer or pneumotachograph), such that the necessary quantity of NO supplemented gas for respiration is produced and infected when needed. This coordinated production of NO for medical uses provides the additional advantage that NO is breathed as it is produced in an oxygen containing gas mixture, allowing less time for NO to oxidize to $NO_2$ before inhalation. When NO is produced, it only lasts for a short period time. After the short period of time, it begins to oxidize into $NO_2$ which, when dissolved in water, forms nitric acid and nitrate salts. If NO is produced long before a user is ready to inhale it, the NO can be oxidized into these toxic products at the time of inspiration. The nitric acid and nitrate salts can damage components of the NO generator as well as the lungs. In combination with spontaneous ventilation, inhalation can be tracked by the EMO of the diaphragm, or a thoracic or abdominal impedance belt, or various airway flow sensors, or taken directly from the ventilator software triggering program, and the electrically generated NO can be injected in the respiratory gas at the onset of inspiration via the nose or trachea with a tube or to mask.

Figure 9A:
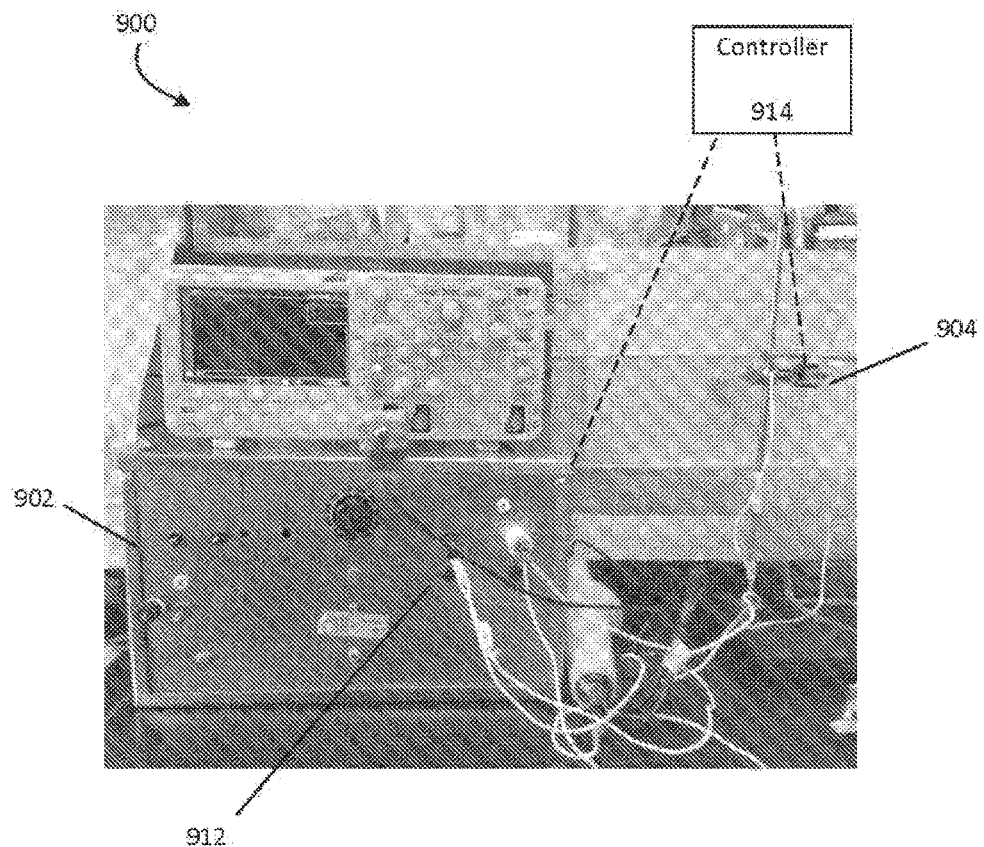
FIG. 9A is a photograph showing an example of a respiratory system for producing NO.
Figure 9B:
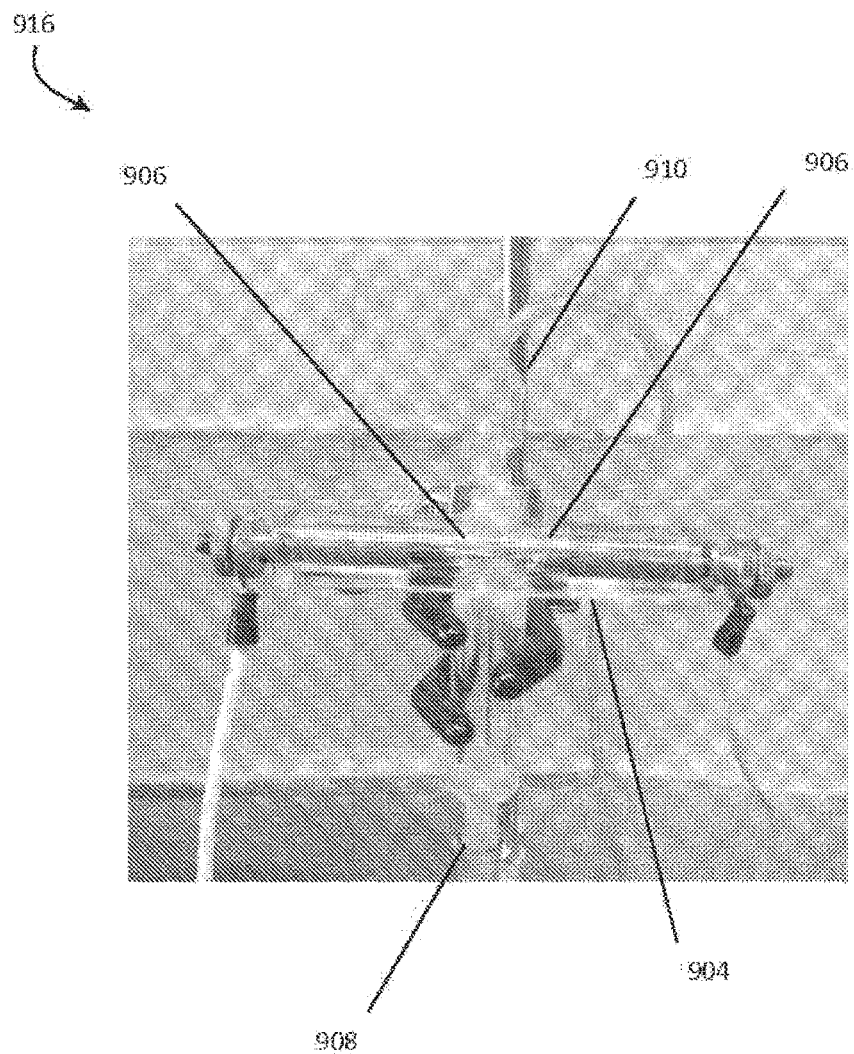
FIG. 9B is a photograph of an NO generator.

FIG. 9A shows an example of a respiratory system 900 for producing NO. In some embodiments, NO is produced electrically under ambient conditions, or hypobaric or hyperbaric conditions. The respiratory system 900 includes power supply 902 and chamber 904. Various components (e.g., an oscilloscope) can make electrical is measurements of the respiratory system 900. In some embodiments, power supply 902 is a battery, and the respiratory system 900 is portable and wearable. FIG. 9B shows an example of an NO generator 916 of respiratory system 900. Reactant gas is provided to chamber 904 through inlet 908, and product gas exits chamber 904 via outlet 910. Power supply 902 is coupled to electrodes 906 in chamber 904 to generate sparks therebetween. Power supply 902 may be operatively coupled to pulse generator 912. Sparks across electrodes 906 form NO in chamber 904 as described herein. For an NO generator such as NO generator 916, a 1 kV to 10 kV spark across electrodes 906 for 10-30 milliseconds that has microampere current, requiring less than 20 W or less than 10 W, based on averaging over the length of the duration of the pulse. Averaging the power consumption over a longer time (e.g., a second) would yield a lower average power consumption (e.g., an order of magnitude or two lower, or about 0.1 W to 1 W).

Systems for producing NO described herein, including respiratory system 900 and others, may also include a controller 914. The controller 914 coordinates triggering of a voltage source to deliver a series of electrical pulses to the electrodes (e.g. electrodes 806), thereby generating NO. The electrodes may be composed of or plated with a material that is capable of optimally producing NO with minimal unwanted toxic by-products. In some examples, the electrodes include a noble metal such as iridium. The controller 914 can be coupled to the pulse generator 912 and at least a portion of the NO generator 916 (e.g., the electrodes 906) and can control parameters such as spark frequency, spark duration, and the like to generate the needed amount of NO and minimum amount of unwanted toxic by-products (e.g., $NO_2$, $O_3$).

The controller 914 can be configured to receive information from one or more sensors in the respiratory system 900. The controller 914 can use the information received from the sensors to determine one or more control parameters for the respiratory system 900. For example, readings from the oxygen level sensor 112 can be used by the controller 914 to determine the one or more control parameters. The respiratory system 900 can include a tidal volume or respiratory gas flow sensor (e.g., a thermistor, a hot wire anemometer) for measuring the volume, timing, and oxygen concentration of inspired gas. The controller may receive information from the ventilator related to is ventilatory time of inspiration or inspired oxygen concentrations. In some examples, the controller 914 can determine control parameters based on one or more of: i) information received from a monitor (e.g., monitor 804 of FIG. 8 for assessing the concentration of components in the product gas or ventilator, such as the NO and $NO_2$ concentration; ii) concentration of components in the reactant gas (e.g., oxygen concentration); iii) operating parameters of the NO generator 900; iv) pressure in the chamber 202 (e.g., especially for embodiments where the NO generator 200, 300 includes a piston 214 for adjusting pressure in the chamber 202); v) flow rate of the reactant gas; vi) actual or expected volume of an inspiration, and vii) whether the produced NO will be diluted with other respiratory gases (e.g., oxygen), to name a few.

The NO generator 900 can provide all or a portion of the product gas at the extremely high breathing frequency of a High Frequency Oscillatory Ventilator (HFOV). The NO generator 900 can provide all or a portion of the product gas to a positive pressure ventilator, an anesthesia machine, a continuous positive airway pressure apparatus, or a manual resuscitator, to name a few.

Adult humans normally breathe from 10-20 times per minute, each breath having a duration of 3-6 seconds. Typically, about one half to one third of the breath's duration is inspiration. On average, each breath has a tidal volume of about 500 ml. In children, each breath typically has less volume, but breathing occurs at a higher rate. Thus, in the average adult, about 10-20 breaths per minute with 1 second inspirations allow intervals for spark generation of about 10 seconds per minute.

The expected volume of an inspiration can be calculated using previous tidal volume measurements. For example, the controller 914 may determine that the expected tidal volume of a subsequent inspiration is going to be the same as the tidal volume measurement for the most recent inspiration. The controller 914 can also average the tidal volumes of several prior inspirations to determine the expected tidal volume of a subsequent inspiration. In some examples, the controller 914 can obtain an expected tidal volume value from the ventilator.

Implementations of controller 914 can include digital electronic circuitry, or computer software, firmware, or hardware, including the structures disclosed in this specification and their structural equivalents, or combinations of one or more of them. An optical or electrical sensor can be incorporated into the device to observe and report the occurrence of the spark(s), and give an alarm if the sparks are not occurring. For example, controller 914 can be a microprocessor based controller (or control system) as well as an electro-mechanical based controller (or control system). Instructions and/or logic in the controller can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated non-transitory signal, e.g., a machine-generated electrical, optical, or electromagnetic signal that is generated to encode information for transmission to suitable receiver apparatus for execution by a data processing apparatus.

Controller 914 can include clients and servers and/or master and slave controllers. A client and server are generally remote from each other and typically interact through a communication network. The relationship of client and server arises by virtue of computer programs running on the respective computers and having a client-server relationship to each other. In some aspects, controller 914 represents a main controller (e.g., master) communicably coupled through communication elements (e.g., wired or wireless) with each of the components of an NO generator. Controller 914 may be configured to adjust parameters related to duration and frequency of the spark based at least in part on the composition of the product gas produced in the chamber.

Figure 10:
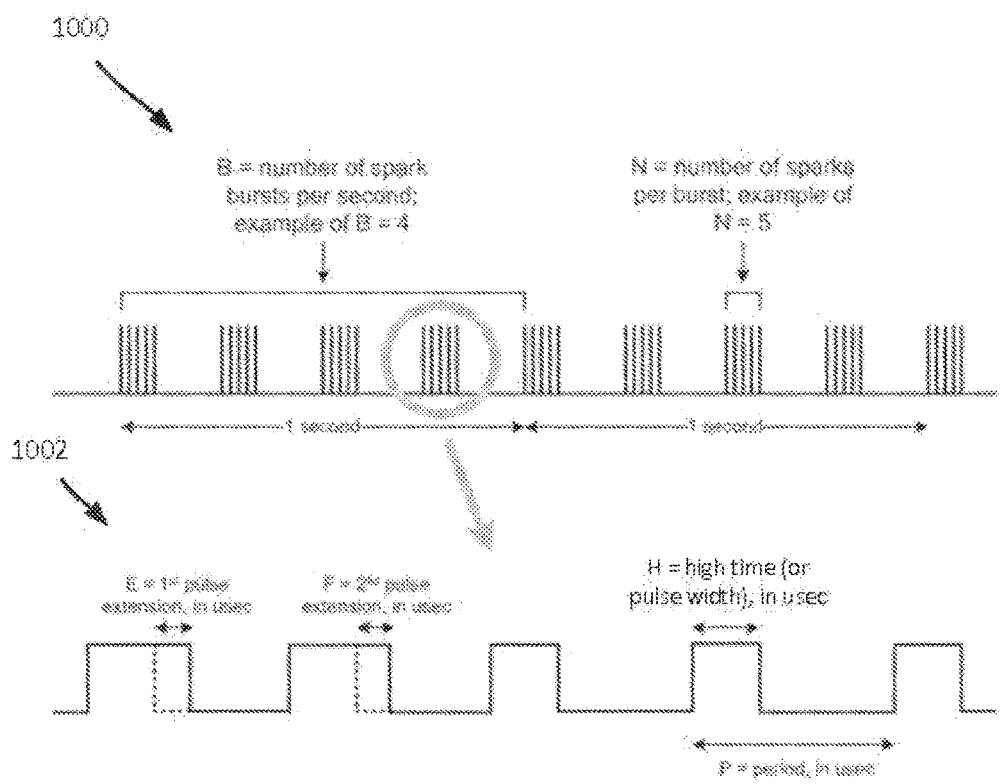
FIG. 10 depicts a representation of a pulse train and a pulse group.

FIG. 10 shows a representation of a pulse train 1000 that is triggered by the controller 914. The controller 914 can determine one or more control parameters to create a pulse train. FIG. 10 also shows zoomed in view of one of the pulse groups 1002 of the pulse train 1000. Electrical pulses are delivered to the electrodes (e.g., electrodes 906), and the electrodes 906 generate a series of sparks (sometimes referred to as electric arcs). The timing of the pulses (and of the resulting sparks) is controlled by the controller 914, and can be optimized to produce the needed amount of NO while producing minimal $NO_2$ and $O_3$. In some examples, the controller 914 causes a greater amount of NO to be produced if the NO will subsequently be diluted with other respiratory gases (e.g., oxygen). Multiple sparks make up a pulse group, and multiple pulse groups make up the pulse train. Thus, the pulse train 1000 initiates the series of electric arcs.

Variables B and N control the overall energy that is created by the electrodes 906. Variable N sets the number of sparks per pulse group, and variable B sets the number of pulse groups per second. The values for B and N influence the amount of NO, $NO_2$, and $O_3$ that is created. The values for B and N also influence how much heat is produced by the electrodes 806. Larger values of either B or N create more NO and cause the electrodes 906 to produce more heat.

Variables E, F, H, and P control the timing of the sparks produced in each pulse group. Variable H is the high time of a pulse (e.g., the amount of time the voltage source is activated for each electrical pulse). The high time is sometimes referred to as the pulse width. High time and pulse width can be visually represented in a graph of a voltage of a pulse over a period of time. The high time and the pulse width are measured from the time the voltage of the pulse exceeds a voltage threshold until the time the voltage of the pulse falls below the voltage threshold, and are generally in the order of microseconds, The longer the voltage source is activated for a particular electric pulse, the larger the visual representation of the width of the particular electric pulse.

P is the amount of time between pulses. Thus, P minus H represents a period of time when no pulses occur (e.g., the voltage source is not active). Larger values of H and smaller values of P result in the electrodes 906 producing more energy. When the electrodes 906 create a spark, plasma is established. The temperature of the plasma is proportional to the amount of energy produced by the electrodes 906. In some examples, for plasma to be produced, the reactant gas has both nitrogen and oxygen content.

B is typically in the range of 5-80 pulse groups per second, N is typically in the range of 1-50 sparks per pulse group, P is typically in the range of 10-800 microseconds, and H is typically in the range of 5-600 microseconds.

The chemical reactions that cause NO and $NO_2$ to be produced are a function of plasma temperature. That is, higher plasma temperatures result in more NO and $NO_2$ being produced. However, the relative proportions of the produced NO and $NO_2$ vary across different plasma temperatures. In some examples, the sparks generated by the first two pulses in a pulse group establish the plasma. The first two sparks can have a high time that is longer than the sparks produced by the rest of the pulses in the pulse group. The amount of time that the first two pulses are extended is represented by variables E and F, respectively. Sparks generated by pulses beyond the first two pulses require less energy to maintain the plasma, so the high time of subsequent pulses (represented by variable H) can be shorter to prevent the plasma temperature from getting too high. For instance, while a relatively high plasma temperature may result in more NO and $NO_2$ being produced, the relatively high plasma temperature may not be ideal for producing the desired proportions of NO and $NO_2$. The material of the electrodes 906 can play a major role in determining the amount of energy needed to generate a particular spark, thus affecting the ratio of $NO_2$/NO produced. In some examples, tungsten electrodes produce a relatively high ratio of $NO_2$/NO, nickel electrodes produced a lower ratio of $NO_2$/NO, and iridium electrodes produce an even lower ratio of $NO_2$/NO, as shown in FIG. 13.

Each spark that is generated creates a particular amount of NO. The NO is diluted in the volume of gas that is produced. To ensure the concentration of NO in the inspired gas is at the expected level, the controller 914 receives information from the tidal volume sensor mentioned above to determine control parameters for maintaining an appropriate inspired NO concentration.

The controller 914 may be configured to communicate with the NO generator wirelessly (e.g., via Bluetooth). The controller 914 can also be configured to communicate with external devices (e.g., a computer, tablet, smart phone, or the like). The external devices can then be used to perform functions of the controller 914 or to aid the controller 914 in performing functions.

In some examples, the controller 914 can disable certain components of the NO generator during, before or after a series of sparks is generated. In some examples, the controller 914 can also include features to: i) detect and cease unintended sparks; ii) confirm that a series of sparks is safe before triggering the series of sparks; iii) verify that timing values are checked against back-up copies of timing values after every series of sparks is generated to detect timing variable corruption; and iv) determine whether back-up copies of timing variables are corrupt.

Results achieved with an NO generator (e.g., NO generator 916) are described with respect to FIGS. 11 through 13.

Figure 11A:
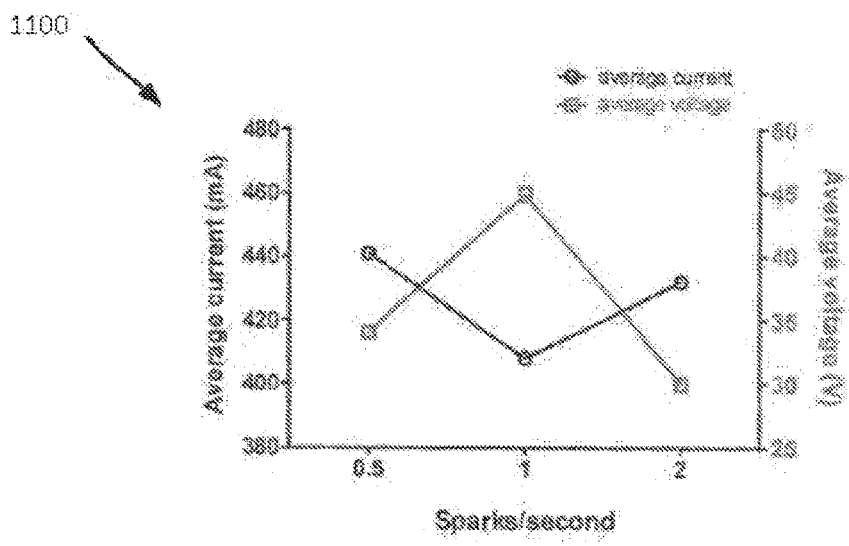
FIG. 11A shows average current and voltage as a function of sparks per second.
Figure 11B:
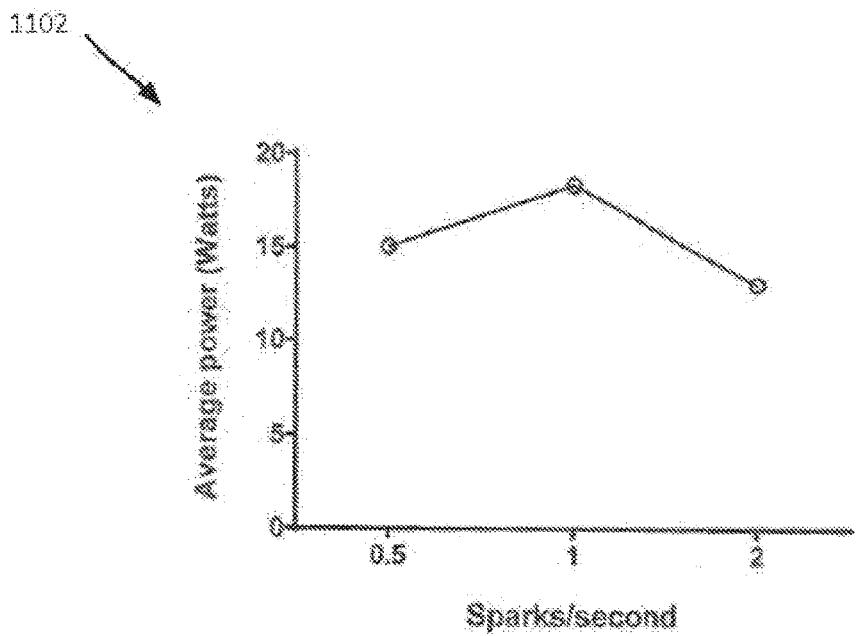
FIG. 11B shows average power as a function of sparks per second.
Figure 12A:
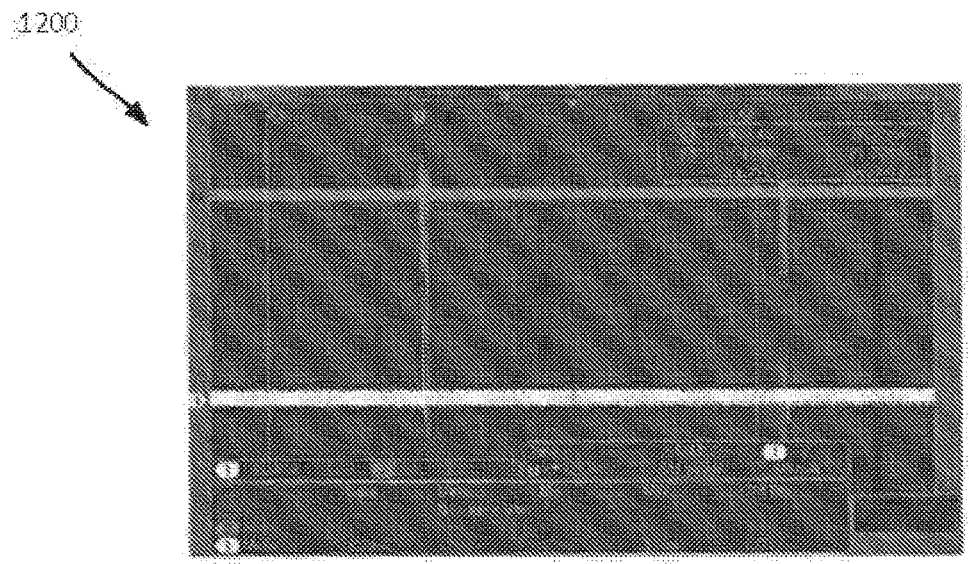
FIGS. 12A-B show tracings of voltage and current during two sparks of a 1 spark/second discharge.
Figure 12B:
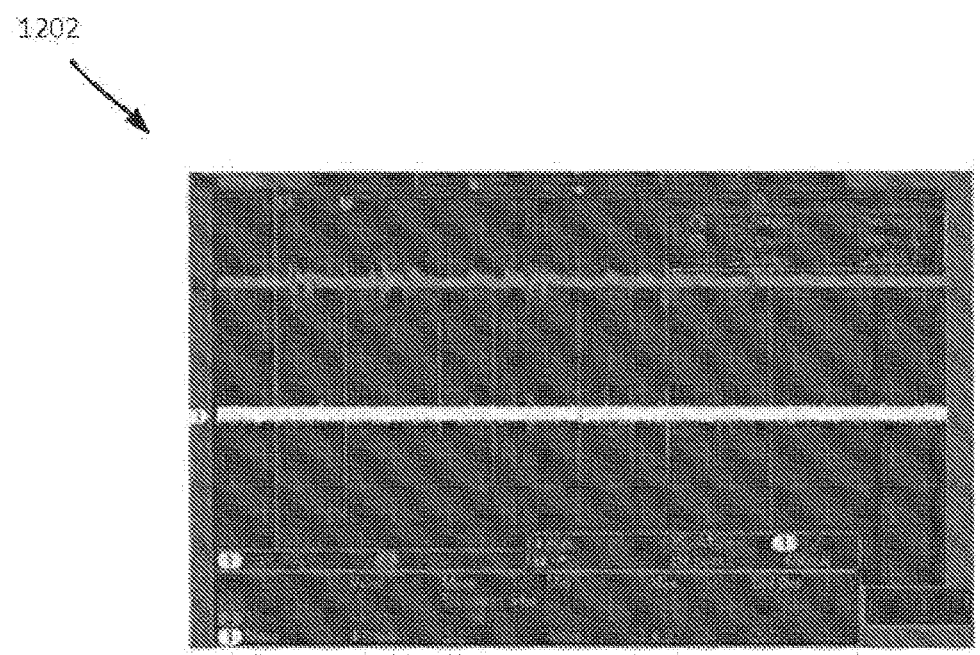

FIG. 11A is an average current and voltage chart 1100 that shows the average current and voltage vs. sparks/second for NO generator 916. FIG. 11B is an average power chart 1102 that shows the average power vs. sparks/second for NO generator 916. Average current and power peak between 0.5 and 2 sparks/second, and average voltage dips over the same range. FIG. 12A shows oscilloscope traces 1200 for voltage (upper trace) and current (lower trace) during 2 sparks of a 1 spark/second discharge. FIG. 12B shows oscilloscope traces 1202 for voltage (upper trace) and current (lower trace) traces for a 1 spark/second discharge with a spark duration (single spark) of 27 msec.

FIG. 13 shows NO and $NO_2$ concentrations from an NO generator (e.g., NO generator 916 of FIG. 9B) using various electrode materials. The test conditions included the use of a ¼" rod, an electrode gap of 2.0 mm, constant air flow at 5 L/min, and a $FiO_2$ of 0.21. For the tungsten electrode, B=40 pulse groups per second, N=30 sparks per pulse group, P=100 microseconds, and H=20 microseconds. For the nickel electrodes, B=35 pulse groups per second, N=40 sparks per pulse group, H=180 microseconds, and P=70 microseconds. For the iridium electrodes, B=35 pulse groups per second, N=40 sparks per pulse group, 11=180 microseconds, and P=80 microseconds.

Figure 14:
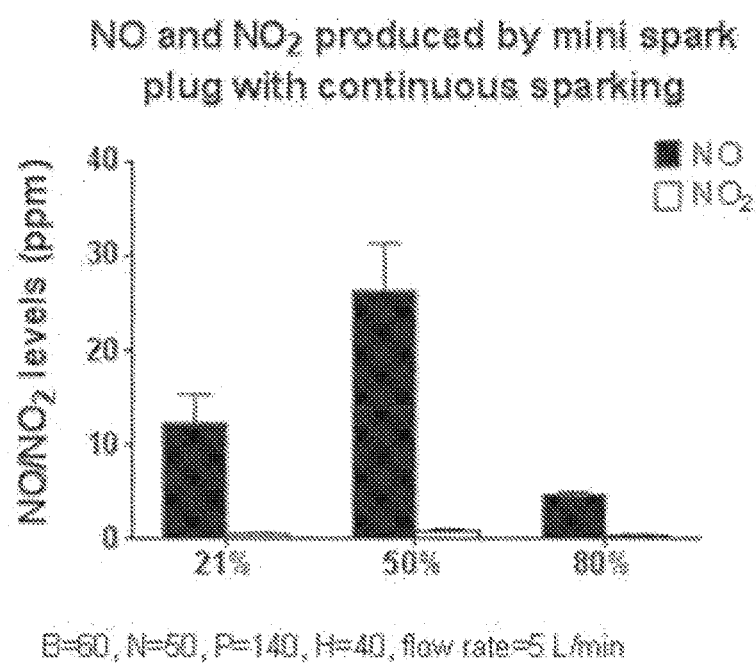
FIG. 14 shows NO and $NO_2$ concentrations at various reactant gas oxygen concentrations.

FIG. 14 shows NO and $NO_2$ concentrations at various reactant gas oxygen concentrations from the NO generator using mini spark plug (Micro Viper Z3 with 6 mm HEX and 10-40 THRD, Rimfire, Benton City, Wash.) that is continuously sparking.

Figure 15:
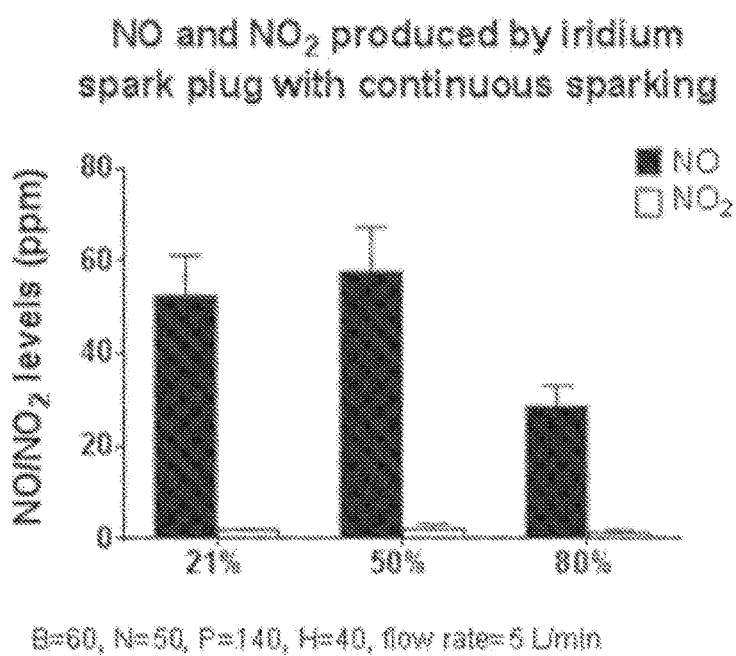
FIG. 15 shows NO and $NO_2$ concentrations at various reactant gas oxygen concentrations.

FIG. 15 shows NO and $NO_2$ concentrations at various reactant gas oxygen concentrations from the NO generator using iridium spark plug (ACDelco 41-101, Waltham, Mass.) that are continuously sparking.

Figure 16:
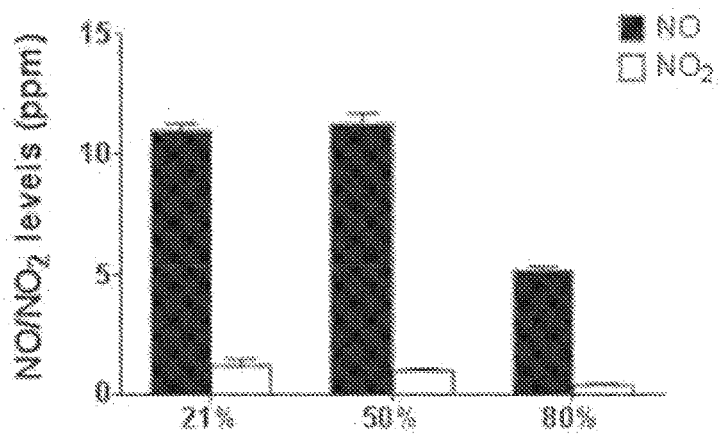
FIG. 16 shows NO and $NO_2$ concentrations at various reactant gas oxygen concentrations.

FIG. 16 shows NO and $NO_2$ concentrations at various reactant gas oxygen concentrations from the NO generator using iridium spark plug with intermittent sparking.

Ozone ($O_3$) is a powerful oxidant that has many industrial and consumer applications related to oxidation. However, its high oxidizing potential causes damage to mucus membranes and respiratory tissues in animals. This makes ozone a potent respiratory hazard and pollutant near ground level. Ozone is formed from atmospheric electrical discharges, and reacts with NO to form nitric dioxide ($NO_2$) and $O_2$ or reacts with $N_2$ to produce NO and $O_2$. In some examples, ozone levels are greater with continuous sparking than with intermittent sparking, and also increase with increasing $O_2$ concentrations.

Figure 17:
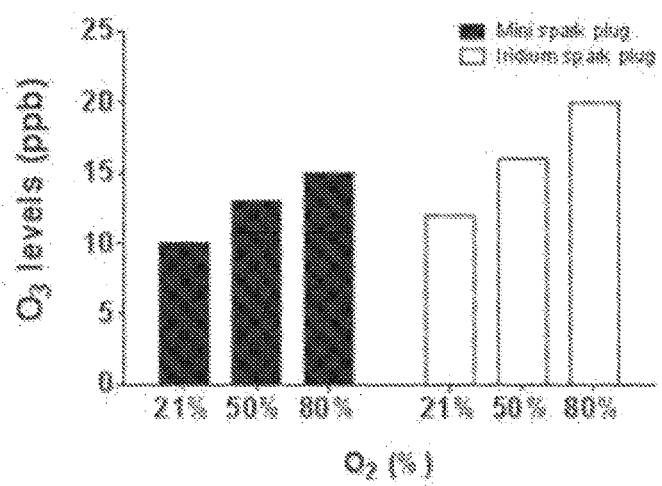
FIG. 17 shows ozone levels at various oxygen concentrations.

FIG. 17 shows $O_3$ levels at various $O_2$ concentrations using mini spark plug and iridium spark plug with continuous sparking. In this example, B=60 pulse groups per second, N=50 sparks per pulse group, P=140 microseconds, H=40 microseconds, and air flow rate is 5 L/min.

Figure 18:
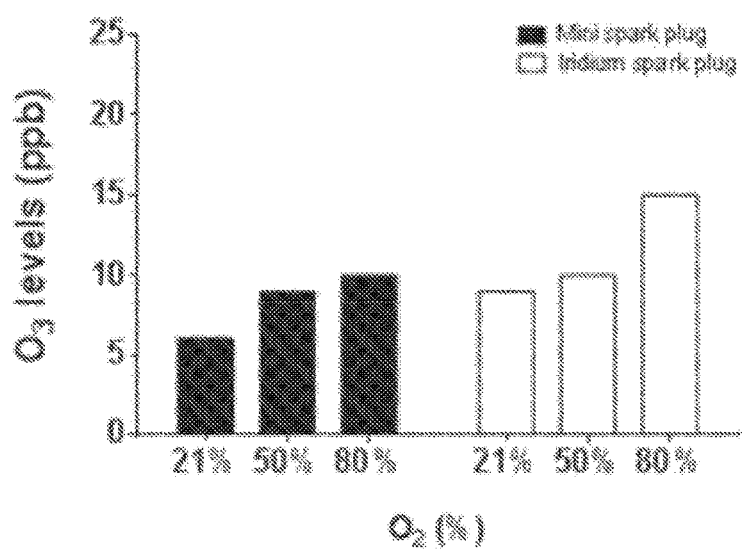
FIG. 18 shows ozone levels at various oxygen concentrations.

FIG. 18 shows $O_3$ levels at various $O_2$ concentrations using mini spark plug and iridium spark plug with intermittent sparking triggered on each breath commencing with inspiration, or shortly before inspiration began. In this example, B=60 pulse groups per second, N=50 sparks per pulse group, P=140 microseconds, H=40 microseconds, and air flow rate is 5 L/min.

Figure 19:
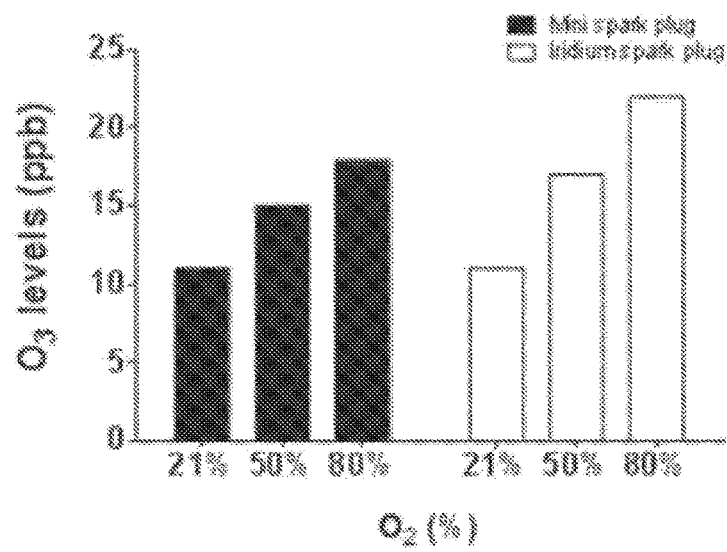
FIG. 19 shows ozone levels at various oxygen concentrations.

FIG. 19 shows $O_3$ levels at various $O_2$ concentrations using mini spark plug and iridium spark plug with continuous sparking. In this example, B=35 pulse groups per second, N=25 sparks per pulse group, P=240 microseconds, H=100 microseconds, and air flow rate is 5 L/min.

Figure 20:
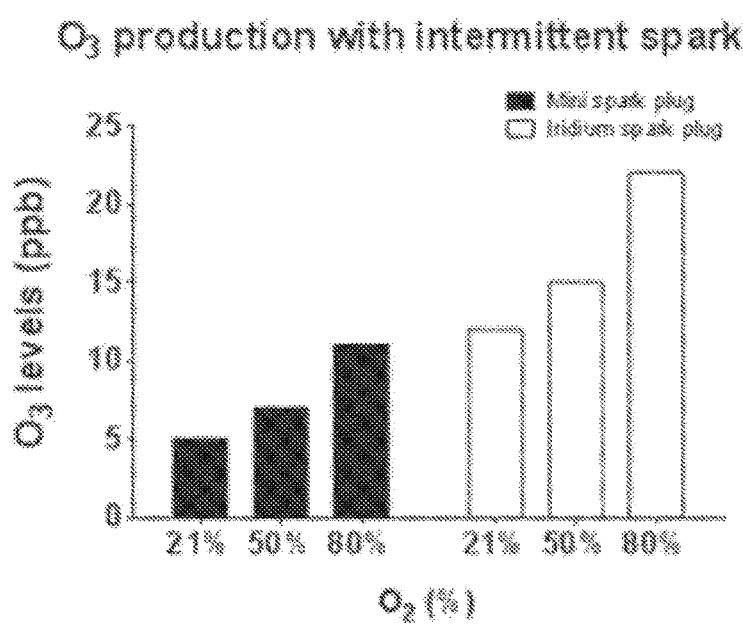
FIG. 20 shows ozone levels at various oxygen concentrations.

FIG. 20 shows $O_3$ levels at various $O_2$ concentrations using mini spark plug and iridium spark plug with intermittent sparking triggered on each breath commencing with inspiration, or shortly before inspiration began. In this example, B=35 pulse groups per second, N=25 sparks per pulse group, P=240 microseconds, H=100 microseconds, and air flow rate is 5 L/min.

Figure 21:
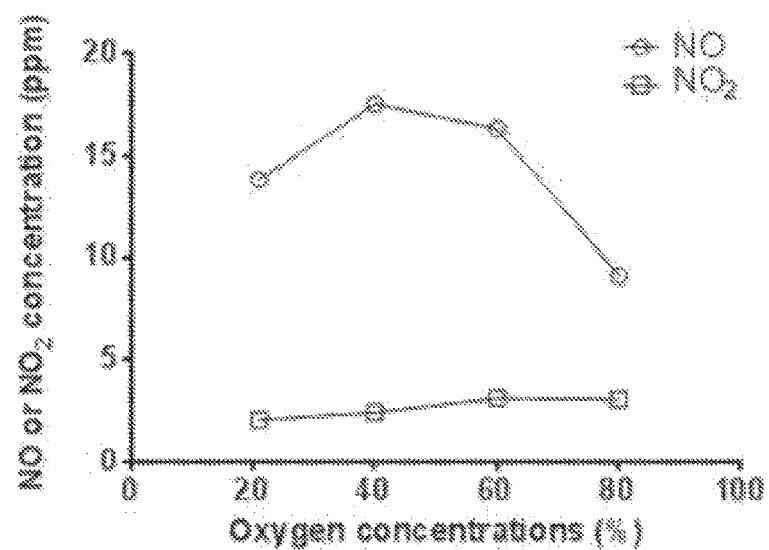
FIG. 21 shows NO and $NO_2$ concentrations at various reactant gas oxygen concentrations.

FIG. 21 shows NO and $NO_2$ concentrations at various reactant gas oxygen concentrations using an oxygen concentrator. In this example, B=5 pulse groups per second, N=25 sparks per pulse group, P=200 microseconds, H=60 microseconds, and air flow rate is 5 L/min.

Figure 22:
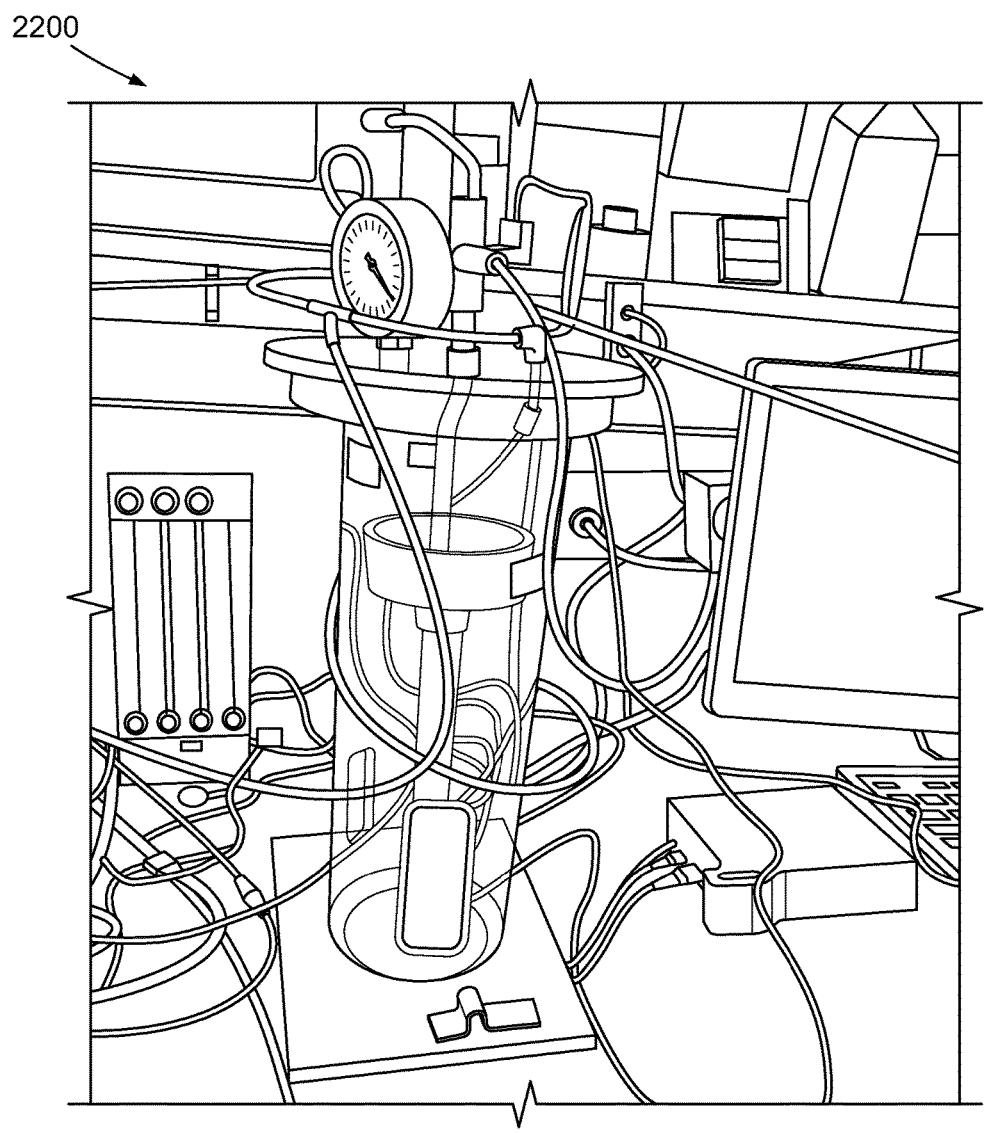
FIG. 22 shows a test setup for measuring NO and $NO_2$ levels in a hypobaric chamber at various atmospheric pressures.
Figure 23:
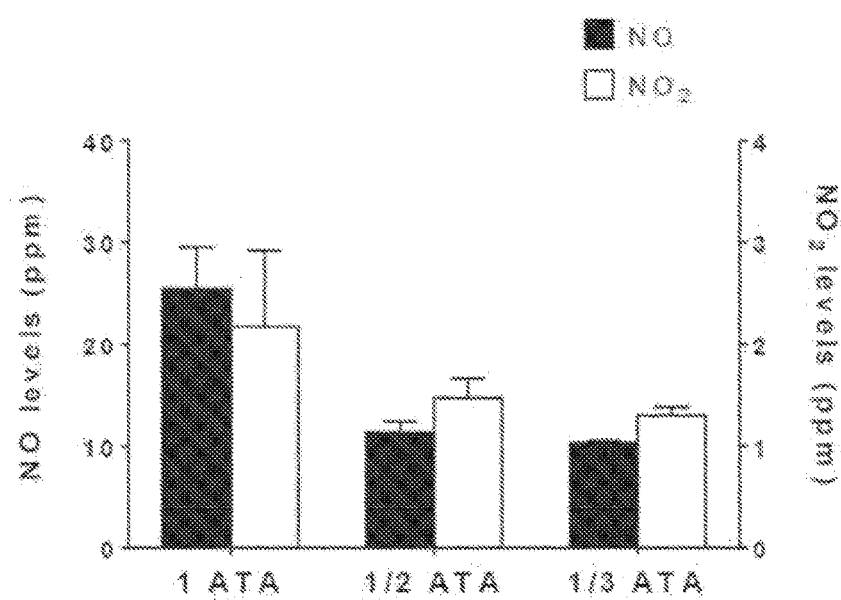
FIG. 23 shows NO and $NO_2$ levels at various atmospheric pressures.

FIG. 22 shows a test setup for measuring NO and $NO_2$ levels in a hypobaric chamber 2200 at various atmospheric pressures. The results of the test are shown in FIG. 23. To create a negative pressure (e.g., ½ ATA, ⅓ ATA) inside the hypobaric chamber 2200, inlet and outlet valves were closed and a piston translated away from the spark plug. The spark plug was then fired for 30 seconds. In this example, B=100 pulse groups per second, N=10 sparks per pulse group, P=140 microseconds, and H=10 microseconds. The piston was then translated toward the spark plug to bring the pressure in the hypobaric chamber 2200 back to 1 ATA. The outlet valve was opened, and gas samples were collected in a 3 L respiratory bag by further translating the piston toward the spark plug. The collected gas samples were analyzed with Sievers NOA i280 immediately after collection.

Figure 24:
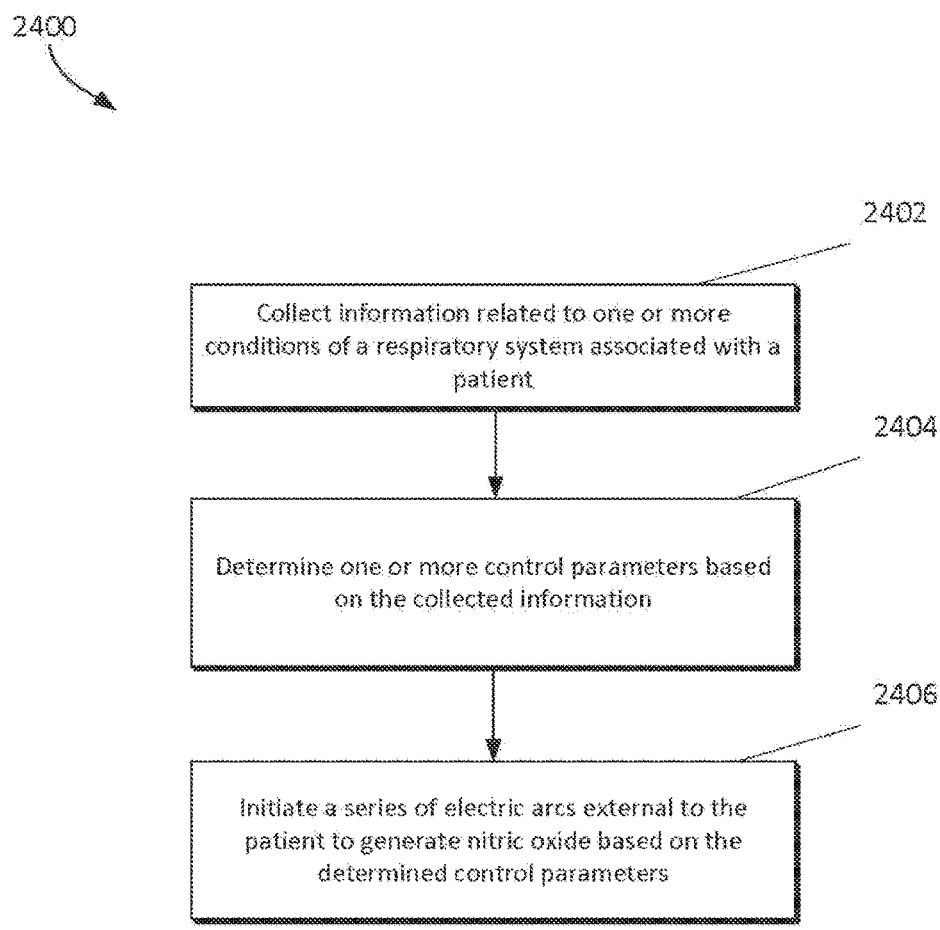
FIG. 24 is a flowchart.

Referring to FIG. 24, a flowchart 2400 represents an arrangement of operations of the controller (e.g., controller 914, shown in FIG. 9A). Typically, the operations are executed by a processor present in the controller. However, the operations may also be executed by multiple processors present in the controller. While typically executed by a single controller, in some arrangements, operation execution may be distributed among two or more controllers.

Operations include collecting 2402 information related to one or more conditions of a respiratory system associated with a patient. For example, one or more sensors of the monitor 804 of FIG. 8 can collect information related to one or more conditions of the respiratory system. In some examples, other sensors in the respiratory system collect information related to one or more conditions of the respiratory system. The conditions associated with the respiratory system include one or more of the oxygen concentration of an input gas (e.g., reactant gas), an input flow rate of the reactant gas, a gas volume and frequency of an inspiration, the pressure in a chamber of the respiratory system, and the oxygen concentration of a product gas before and after admixture in the respiratory system. Operations also include determining 2404 one or more control parameters based on the collected information. For example, the controller 914 of FIG. 9A can determine one or more control parameters. The control parameters may create a pulse train. Operations also include initiating 2406 a series of electric arcs external to the patient to generate nitric oxide based on the determined control parameters. For example, the electrodes 906 of FIG. 9B can initiate a series of electric arcs external to the patient to generate nitric oxide based on the determined control parameters. The control parameters may control the timings of the series of electric arcs. In some examples, the conditions associated with the respiratory system also include the amounts of NO and $NO_2$ generated by the series of electric arcs (e.g., amounts of NO and $NO_2$ previously generated.

Figure 25:
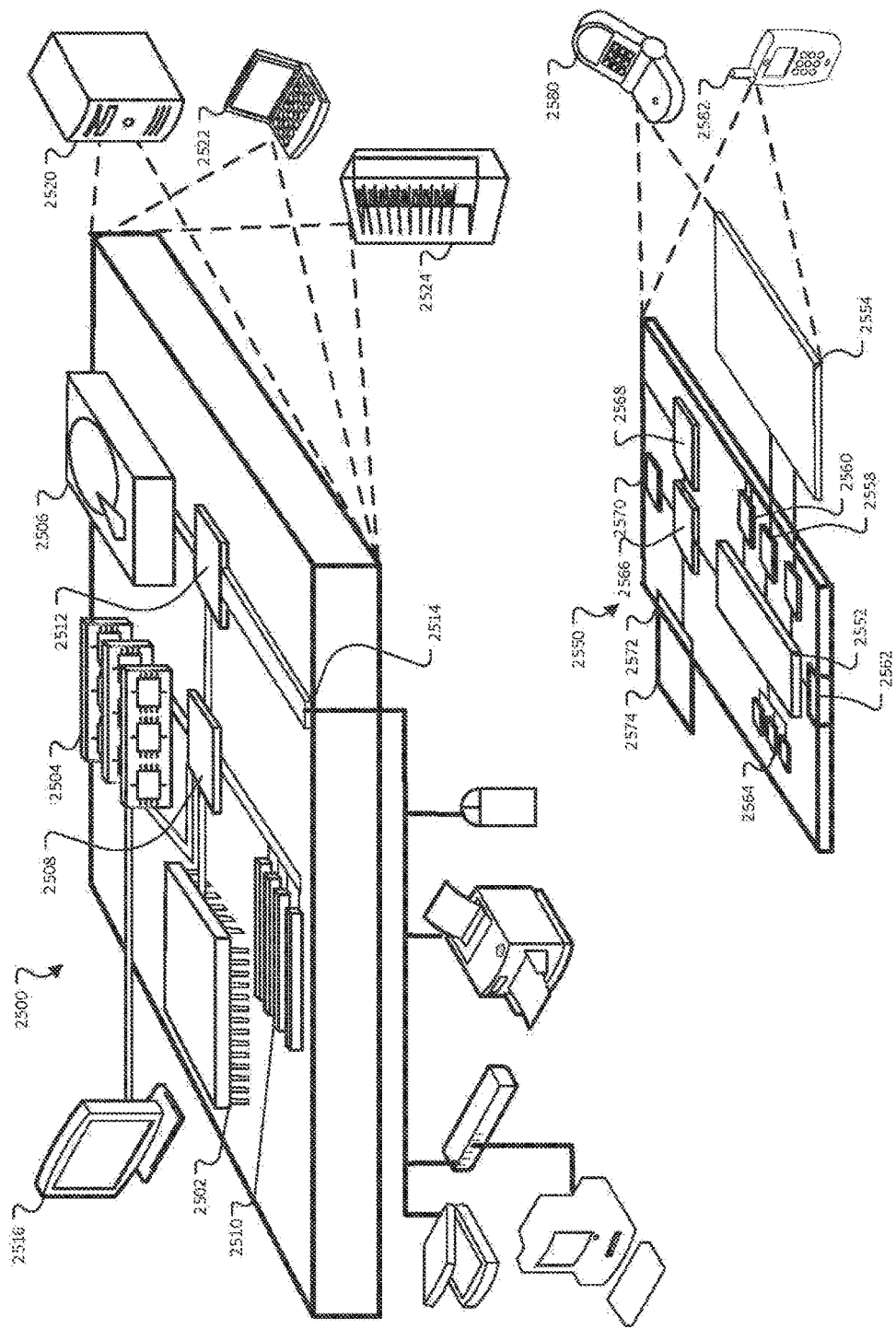
FIG. 25 illustrates an example of a computing device and a mobile computing device that can be used to implement the operations and techniques described herein.

FIG. 25 shows an example of example computer device 2500 and example mobile computer device 2550, which can be used to implement the operations and techniques described herein. For example, a portion or all of the operations of a controller (e.g., controller 914 of FIG. 9A) may be executed by the computer device 2500 and/or the mobile computer device 2550. Computing device 2500 is intended to represent various forms of digital computers, including, e.g., laptops, desktops, workstations, personal digital assistants, servers, blade servers, mainframes, and other appropriate computers. Computing device 2550 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 2500 includes processor 2502, memory 2504, storage device 2506, high-speed interface 2508 connecting to memory 2504 and high-speed expansion ports 2510, and low speed interface 2512 connecting to low speed bus 2514 and storage device 2506. Each of components 2502, 2504, 2506, 2508, 2510, and 2512, are interconnected using various busses, and can be mounted on a common motherboard or in other manners as appropriate. Processor 2502 can process instructions for execution within computing device 2500, including instructions stored in memory 2504 or on storage device 2506 to display graphical data for a GUI on an external input/output device, including, e.g., display 2516 coupled to high speed interface 2508. In other implementations, multiple processors and/or multiple buses can be used, as appropriate, along with multiple memories and types of memory. Also, multiple computing devices 2500 can be connected, with each device providing portions of the necessary operations (e.g., as a server bank, a group of blade servers, or a multi-processor system).

Memory 2504 stores data within computing device 2500. In one implementation, memory 2504 is a volatile memory unit or units. In another implementation, memory 2504 is a non-volatile memory unit or units. Memory 2504 also can be another form of computer-readable medium, including, e.g., a magnetic or optical disk.

Storage device 2506 is capable of providing mass storage for computing device 2500. In one implementation, storage device 2506 can be or contain a computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 2504, storage device 2506, memory on processor 2502, and the like.

High-speed controller 2508 manages bandwidth-intensive operations for computing device 2500, while low speed controller 2512 manages lower bandwidth-intensive operations. Such allocation of functions is an example only. In one implementation, high-speed controller 2508 is coupled to memory 2504, display 2516 (e.g., through a graphics processor or accelerator), and to high-speed expansion ports 2510, which can accept various expansion cards (not shown). In the implementation, low-speed controller 2512 is coupled to storage device 2506 and low-speed expansion port 2514. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

Computing device 2500 can be implemented in a number of different forms, as shown in the figure. For example, it can be implemented as standard server 2520, or multiple times in a group of such servers. It also can be implemented as part of rack server system 2524. In addition or as an alternative, it can be implemented in a personal computer including, e.g., laptop computer 2522. In some examples, components from computing device 2500 can be combined with other components in a mobile device (not shown), including, e.g., device 2550. Each of such devices can contain one or more of computing device 2500, 2550, and an entire system can be made up of multiple computing devices 2500, 2550 communicating with each other.

Computing device 2550 includes processor 2552, memory 2564, an input/output device including, e.g., display 2554, communication interface 2566, and transceiver 2568, among other components. Device 2550 also can be provided with a storage device, including, e.g., a microdrive or other device, to provide additional storage. Each of components 2550, 2552, 2564, 2554, 2566, and 2568, are interconnected using various buses, and several of the components can be mounted on a common motherboard or in other manners as appropriate.

Processor 2552 can execute instructions within computing device 2550, including instructions stored in memory 2564. The processor can be implemented as a chipset of chips that include separate and multiple analog and digital processors. The processor can provide, for example, for coordination of the other components of device 2550, including, e.g., control of user interfaces, applications run by device 2550, and wireless communication by device 2550.

Processor 2552 can communicate with a user through control interface 2558 and display interface 2556 coupled to display 2554. Display 2554 can be, for example, a TFT LCD (Thin-Film-Transistor Liquid Crystal Display) or an OLED (Organic Light Emitting Diode) display, or other appropriate display technology. Display interface 2556 can comprise appropriate circuitry for driving display 2554 to present graphical and other data to a user. Control interface 2558 can receive commands from a user and convert them for submission to processor 2552. In addition, external interface 2562 can communicate with processor 2542, so as to enable near area communication of device 2550 with other devices. External interface 2562 can provide, for example, for wired communication in some implementations, or for wireless communication in other implementations, and multiple interfaces also can be used.

Memory 2564 stores data within computing device 2550. Memory 2564 can be implemented as one or more of a computer-readable medium or media, a volatile memory unit or units, or a non-volatile memory unit or units. Expansion memory 2574 also can be provided and connected to device 2550 through expansion interface 2572, which can include, for example, a SIMM (Single In Line Memory Module) card interface. Such expansion memory 2574 can provide extra storage space for device 2550, or also can store applications or other data for device 2550. Specifically, expansion memory 2574 can include instructions to carry out or supplement the processes described above, and can include secure data also. Thus, for example, expansion memory 2574 can be provided as a security module for device 2550, and can be programmed with instructions that permit secure use of device 2550. In addition, secure applications can be provided through the SIMM cards, along with additional data, including, e.g., placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., those described above. The data carrier is a computer- or machine-readable medium, including, e.g., memory 2564, expansion memory 2574, and/or memory on processor 2552, which can be received, for example, over transceiver 2568 or external interface 2562.

Device 2550 can communicate wirelessly through communication interface 2566, which can include digital signal processing circuitry where necessary. Communication interface 2566 can provide for communications under various modes or protocols, including, e.g., GSM voice calls, SMS, EMS, or MMS messaging, CDMA, TDMA, PDC, WCDMA, CDMA2000, or CPRS, among others. Such communication can occur, for example, through radio-frequency transceiver 2568. In addition, short-range communication can occur, including, e.g., using a Bluetooth®, WiFi, or other such transceiver (not shown). In addition, GPS (Global Positioning System) receiver module 2570 can provide additional navigation- and location-related wireless data to device 2550, which can be used as appropriate by applications running on device 2550. Sensors and modules such as cameras, microphones, compasses, accelerators (for orientation sensing), etc. maybe included in the device.

Device 2550 also can communicate audibly using audio codec 2560, which can receive spoken data from a user and convert it to usable digital data. Audio codec 2560 can likewise generate audible sound for a user, including, e.g., through a speaker, e.g., in a handset of device 2550. Such sound can include sound from voice telephone calls, can include recorded sound (e.g., voice messages, music files, and the like) and also can include sound generated by applications operating on device 2550.

Computing device 2550 can be implemented in a number of different forms, as shown in the figure. For example, it can be implemented as cellular telephone 2580. It also can be implemented as part of smartphone 2582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying data to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a user interface or a Web browser through which a user can interact with an implementation of the systems and techniques described here), or a combination of such back end, middleware, or front end components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

What is claimed is:

1. An apparatus comprising:
   an inlet configured to receive a reactant gas containing nitrogen and oxygen;
   an outlet configured to provide a product gas containing nitric oxide, wherein the product gas is formed by a synthesis of the reactant gas;
   a reaction chamber arranged between the inlet and the outlet;
   one or more pairs of electrodes within the reaction chamber and configured to initiate a series of electric arcs to synthesize the reactant gas to the product gas;
   a sensor configured to measure a flow of a gas in a ventilator into which the product gas is provided through the outlet; and
   a controller in communication with the one or more pairs of electrodes and the sensor, the controller being configured to:
      adjust at least one of a pulse width, pulse period, pulse count per pulse group, pulse groups per second, energy generated by the one or more pairs of electrodes, arc frequency, arc current, and a voltage supplied to the one or more pairs of electrodes based on the measured flow to control a concentration of nitric oxide in the product gas.

2. The apparatus of claim 1, wherein the one or more pairs of electrodes include a noble metal.

3. The apparatus of claim 1, wherein the one or more pairs of electrodes include iridium.

4. The apparatus of claim 1, further comprising a filter arranged upstream of the inlet.

5. The apparatus of claim 1, wherein the controller adjusts the at least one of a pulse width, pulse period, pulse count per pulse group, pulse groups per second, energy generated by the one or more pairs of electrodes, arc frequency, arc current, and a voltage to minimize a concentration of NO2 in the product gas.

6. The apparatus of claim 1, wherein the controller controls the nitric oxide concentration of the product gas with the flow rate of the reactant gas.

7. An apparatus comprising:
   an inlet configured to receive a reactant gas containing nitrogen and oxygen;
   an outlet configured to provide a product gas containing nitric oxide, wherein the product gas is formed by a synthesis of the reactant gas;
   a reaction chamber arranged between the inlet and the outlet;
   one or more pairs of electrodes within the reaction chamber and configured to initiate electric arcs to synthesize the reactant gas to the product gas;
   a sensor configured to measure a flow of a gas in a ventilator into which the product gas is provided through the outlet; and
   a controller in communication with the one or more pairs of electrodes and the sensor, the controller being configured to:
      adjust one or more conditions within the reaction chamber based on the measured flow of gas in the ventilator to control a concentration of nitric oxide in the product gas.

8. The apparatus of claim 7, wherein the one or more pairs of electrodes include a noble metal.

9. The apparatus of claim 7, wherein the one or more pairs of electrodes include iridium.

10. The apparatus of claim 7, further comprising a filter arranged upstream of the inlet.

11. The apparatus of claim 7, wherein the gas into which the product gas is provided flows into an inspiratory limb associated with the ventilator.

12. The apparatus of claim 7, wherein the one or more conditions within the reaction chamber include at least one of a pulse width, pulse period, pulse count per pulse group, pulse groups per second, energy generated by the one or more pairs of electrodes, arc frequency, arc current, and a voltage supplied to the one or more pairs of electrodes based on the measured flow.

13. The apparatus of claim 7, wherein the one or more conditions within the reaction chamber include a rate of reactant gas flow through the reaction chamber.

14. The apparatus of claim 7, wherein the one or more conditions within the reaction chamber include a pressure associated with the reaction chamber.

15. The apparatus of claim 7, wherein the controller adjusts the one or more conditions within the reaction chamber to minimize a concentration of NO2 in the product gas.

16. An apparatus comprising:
   an inlet configured to receive a reactant gas containing nitrogen and oxygen;
   an outlet configured to provide a product gas containing nitric oxide, wherein the product gas is formed by a synthesis of the reactant gas;
   a reaction chamber arranged between the inlet and the outlet;
   one or more pairs of electrodes within the reaction chamber and configured to initiate a series of electric arcs to synthesize the reactant gas to the product gas, the one or more pairs of electrodes include iridium to minimize a concentration of $NO_2$ in the product gas;
   a sensor configured to measure a flow of a gas in a ventilator into which the product gas is provided through the outlet; and
   a controller in communication with the one or more pairs of electrodes and the sensor, the controller being configured to adjust one or more conditions within the reaction chamber to control a concentration of nitric oxide in the product gas based on the measured flow to control a concentration of nitric oxide in the product gas.

17. The apparatus of claim 16, the one or more conditions within the reaction chamber include a rate of reactant gas flow through the reaction chamber.

18. A method for generating nitric oxide, the method comprising:

providing a reactant gas containing nitrogen and oxygen to a reaction chamber having one or more pairs of electrodes therein, initiating a series of electric arcs in the reaction chamber to synthesize the reactant gas to a product gas containing nitric oxide;

measuring a flow of a gas in a ventilator into which the product gas is provided; and adjusting one or more conditions within the reaction chamber based on the measured flow of gas in the ventilator to control a concentration of nitric oxide in the product gas.

19. The method of claim 18, wherein the one or more conditions within the reaction chamber include at least one of a pulse width, pulse period, pulse count per pulse group, pulse groups per second, energy generated by the one or more pairs of electrodes, arc frequency, arc current, and a voltage supplied to the one or more pairs of electrodes based on the measured flow to control the series of electrical arcs to control a concentration of nitric oxide in the product gas.

20. The method of claim 18, wherein the one or more conditions within the reaction chamber include the rate of air flow through the reaction chamber.

21. The method of claim 18, wherein the one or more conditions within the reaction chamber include a pressure associated with the reaction chamber.

* * * * *

UNITED STATES PATENT AND TRADEMARK OFFICE
CERTIFICATE OF CORRECTION

PATENT NO. : 10,279,139 B2
APPLICATION NO. : 15/880018
DATED : May 7, 2019
INVENTOR(S) : Warren M. Zapol et al.

It is certified that error appears in the above-identified patent and that said Letters Patent is hereby corrected as shown below:

In the Specification

Column 3, Line 60, "level to of nitrogen" should be --level of nitrogen--.

Column 10, Line 5, "infected" should be --injected--.

Column 10, Line 23, "tube or to mask" should be --tube or mask--.

Column 10, Line 29, "electrical is measurements" should be --electrical measurements--.

Column 11, Line 7, "related to is ventilatory" should be --related to ventilatory--.

Column 14, Line 8, "11-180" should be --H-180--.

Column 15, Line 45, "generated." should be --generated).--.

Column 18, Line 1, "CPRS" should be --GPRS--.

Signed and Sealed this
Twenty-fifth Day of June, 2019

Andrei Iancu
*Director of the United States Patent and Trademark Office*